United States Patent [19]

Parma et al.

[11] Patent Number: 5,622,828

[45] Date of Patent: Apr. 22, 1997

[54] HIGH-AFFINITY OLIGONUCLEOTIDE LIGANDS TO SECRETORY PHOSPHOLIPASE A2 (SPLA$_2$)

[75] Inventors: David H. Parma; Larry Gold, both of Boulder, Colo.

[73] Assignee: Nexstar Pharmaceuticals, Inc., Boulder, Colo.

[21] Appl. No.: 399,412

[22] Filed: Mar. 6, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and Ser. No. 964,624, Oct. 21, 1992, Pat. No. 5,496,938.

[51] Int. Cl.$^6$ .............................. C12P 19/34; C12Q 1/68; C07H 21/02; C07H 21/04

[52] U.S. Cl. ............................ 435/6; 435/91.2; 536/22.1; 935/77; 935/78

[58] Field of Search ................. 435/6, 91.2; 536/22.1; 935/77, 78

[56] References Cited

FOREIGN PATENT DOCUMENTS 9214843  9/1992  WIPO .................................. 435/6

*Primary Examiner*—Stephanie W. Zitomer

[57] ABSTRACT

This invention discloses high-affinity oligonucleotide ligands to human secretory phospholipase A2 (sPLA$_2$), specifically RNA ligands having the ability to bind to sPLA$_2$, and the methods for obtaining such ligands.

11 Claims, No Drawings

5,622,828

HIGH-AFFINITY OLIGONUCLEOTIDE LIGANDS TO SECRETORY PHOSPHOLIPASE A2 (SPLA$_2$)

RELATED APPLICATIONS

This application is a Continuation-in-Part of U.S. patent Ser. No. 714,131 filed Jun. 10, 1991, now U.S. Pat. No. 5,475,096, issued Dec. 12, 1995, entitled *Nucleic Acid Ligands*, which is a Continuation-in Part of U.S. patent application Ser. No. 07/536,428, filed Jun. 11, 1990, entitled *Systematic Evolution of Ligands by Exponential Enrichment*, now abandoned, and U.S. patent Ser. No. 964,624, filed Oct. 21, 1992, now U.S. Pat. No. 5,496,938, issued Mar. 5, 1996, entitled *Nucleic Acid Ligands to HIV-RT and HIV-1 Rev,* now U.S. Pat. No. 5,496,938.

FIELD OF THE INVENTION

Described herein are methods for identifying and preparing high-affinity nucleic acid ligands to secretory phospholipase A2 (sPLA$_2$). The method utilized herein for identifying such nucleic acid ligands is called SELEX, an acronym for Systematic Evolution of Ligands by Exponential enrichment. Specifically disclosed herein are high-affinity nucleic acid ligands. The invention includes high-affinity RNA ligands which bind to sPLA$_2$ and inhibit the enzymatic activity of sPLA$_2$.

BACKGROUND OF THE INVENTION

Inflammation is a local response to tissue damage or foreign material which is designed to isolate and/or destroy injured tissues and foreign substances. Uncontrolled inflammatory responses may irreparably damage host tissue, as in the chronic inflammation of rheumatoid arthritis or lead to multiple organ failure and death as in the systemic inflammation of septic shock.

Eicosanoids are metabolic products of the essential fatty acid, arachadonic acid and are known to play a central role in the inflammatory response. Arachadonic acid is an integral component of cell membranes where it is commonly found as an sn-2 acyl or akyl ester of 3-sn-phosphoglycerides. Phospholipase A2 (PLA$_2$) is a class of enzymes that specifically catalyze the hydrolysis of the sn-2 acyl or alkyl ester of phosphoglycerides, producing equimolar quantities of lysophospholipids and free fatty acids. The PLA$_2$ catalyzed hydrolysis of one such membrane phospholipid, alkyl-arachidonyl-glycerophosphatidylcholine, yields free arachidonic acid and lyso-platelet activating factor (lyso-PAF), the precursor of PAF, in equimolar amounts. Since the availability of free arachidonic acid is rate limiting for eicosanoid synthesis, the pro-inflammatory role of PLA$_2$ is thought to be the consequence of its role in arachadonic acid metabolism.

Three mammalian PLA$_2$ enzymes are known. Pancreatic PLA$_2$ is related to the type I PLA$_2$ from the venom of Elapidae and Hydrophide both in primary and tertiary structure. A digestive enzyme, synthesized as a proenzyme in the pancreas, it is unlikely to play a central role in inflammatory conditions.

Two non-pancreatic mammalian enzymes have been described. One is a high molecular weight intracellular enzyme. The other is a soluble enzyme, sPLA$_2$, and is of particular interest because it has been isolated from inflammatory exudates, such as synovial fluid (Seilhamer et al. (1989) J. Biol. Chem. 264: 5335–5338) and from platelets (Kramer et al. (1989) J. Bio. Chem. 264: 5768–5775). sPLA$_2$ is known by several equivalent names, including secretory phospholipase A$_2$, soluble phospholipase A$_2$ and synovial phospholipase A2, all of which can be used interchangeably. This enzyme, which has been sequenced, has a molecular weight of 14 kD, a pI>10 and is homologous to type II PLA$_2$ from the venoms of Crotalidae and Viperidac (Kramer et al. (1989) supra; Scott et al. (1991) Science 254: 1007; Wery et al. (1991) Nature 352: 79–82).

The involvement of sPLA$_2$ in the inflammatory response is supported by two types of data. First, elevated levels of serum PLA$_2$ activity have been observed in diseases such as endotoxemia (Vadas and Hay (1983) Can. J. Physiol. Pharmacol. 61: 561–566), sepsis (Vadas (1984) J. Lab. Clin. Med. 104: 873–881; Nevalainen et al. (1992) Clin. Chem. 38: 1824–1829), rheumatoid arthritis (Pruzanski et al. (1988) J. Rheumatol. 15: 1351–1355), pancreatitis (Nevalainen et al. (1993) Gut 34: 1133–1136) and uremia (Costello et al. (1990) Clin. Chem. 36: 198–200) and in some studies correlate with severity and outcome. One of the best documented cases is acute pancreatitis in which sPLA$_2$ immuno-reactive activity, but not pancreatic PLA$_2$ immuno-reactive activity, is correlated with serum PLA$_2$ enzymatic activity. The duration of the elevated levels is longer for the more severe necrotizing pancreatitis than the less severe oedmatous form (Nevalainen et al. (1993) supra).

Second, in both animal and tissue models (Snyder et al. (1993) J. Pharmacol. and Therapeutics 266: 1147–1155), the introduction of sPLA$_2$ results in an inflammatory like response.

The isolation of specific antagonists to sPLA$_2$ would have multiple uses. First, sPLA$_2$ ligands would provide a useful tool for defining the enzyme's role in inflammatory responses and in diagnosing various inflammatory conditions. Second, sPLA$_2$ antagonists would be useful as an anti-inflammatory therapeutic. Given the cationic nature of sPLA$_2$ and the specificity of high affinity oligonucleotide ligands, SELEX technology is well suited for the isolation of sPLA$_2$ antagonists which would not cross react with pancreatic or high molecular weight PLA2s. The present invention demonstrates the successful isolation of high-affinity oligonucleotide antagonists to sPLA$_2$.

BRIEF SUMMARY OF THE INVENTION

The present invention includes methods of identifying and producing nucleic acid ligands to secretory phospholipase A2 (sPLA$_2$) and the nucleic acid ligands so identified and produced. More particularly, RNA sequences are provided that are capable of binding specifically to sPLA$_2$.

Further included in this invention is a method of identifying nucleic acid ligands and nucleic acid ligand sequences to sPLA$_2$ comprising the steps of (a) preparing a candidate mixture of nucleic acids, (b) partitioning between members of said candidate mixture on the basis of affinity to sPLA$_2$, and (c) amplifying the selected molecules to yield a mixture of nucleic acids enriched for nucleic acid sequences with a relatively higher affinity for binding to sPLA$_2$.

More specifically, the present invention includes the RNA ligands to sPLA$_2$ identified according to the above-described method, including those ligands listed in Table 2. Also included are RNA ligands to sPLA$_2$ that are substantially homologous to any of the given ligands and that have substantially the same ability to bind sPLA$_2$ and antagonize sPLA$_2$ activity. Further included in this invention are RNA ligands to sPLA$_2$ that have substantially the same structural form as the ligands presented herein and that have substantially the same ability to bind sPLA$_2$ and antagonize sPLA$_2$ activity.

The present invention also includes modified nucleotide sequences based on the RNA ligands identified herein and mixtures of the same.

DETAILED DESCRIPTION OF THE INVENTION

This application describes high-affinity nucleic acid ligands to sPLA$_2$ identified through the method known as SELEX. SELEX is described in U.S. patent application Ser. No. 07/536,428, entitled *Systematic Evolution of Ligands by EXponential Enrichment*, now abandoned, U.S. patent application Ser. No. 07/714,131, filed Jun. 10, 1991, entitled *Nucleic Acid Ligands*, now U.S. Pat. No. 5,475,096, U.S. patent application Ser. No. 07/931,473, filed Aug. 17, 1992, entitled *Nucleic Acid Ligands*, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with a lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of sPLA$_2$. In the Example section below, the experimental parameters used to isolate and identify the nucleic acid ligands to sPLA$_2$ are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled *Nucleic Acid Ligands to HIV-RT and HIV-1 Rev*, is specifically incorporated herein by reference.

In the present invention, a SELEX experiment was performed in search of RNA with specific high affinity for sPLA$_2$ from a degenerate library containing 30 or 50 random positions (30N or 50N). This invention includes the specific RNA ligands to sPLA$_2$ shown in Table 2 (SEQ ID Nos.:10–122), identified by the methods described in Examples 1 and 2. The scope of the ligands covered by this invention extends to all nucleic acid ligands of sPLA$_2$, modified and unmodified, identified according to the SELEX procedure. More specifically, this invention includes nucleic acid sequences that are substantially homologous to the ligands shown in Table 2. By substantially homologous it is meant a degree of primary sequence homology in excess of 70%, most preferably in excess of 80%. A review of the sequence homologies of the ligands of sPLA$_2$ shown in Table 2 shows that sequences with little or no primary homology may have substantially the same ability to bind sPLA$_2$. For these reasons, this invention also includes nucleic acid ligands that have substantially the same ability to bind sPLA$_2$ as the nucleic acid ligands shown in Table 2. Substantially the same ability to bind sPLA$_2$ means that the affinity is within a few orders of magnitude of the affinity of the ligands described herein. It is well within the skill of those of ordinary skill in the art to determine whether a given sequence—substantially homologous to those specifically described herein—has substantially the same ability to bind sPLA$_2$.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled *High Affinity Nucleic Acid Ligands Containing Modified Nucleotides*, now abandoned, specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the $sPLA_2$ protein described herein are useful as pharmaceuticals and as diagnostic reagents.

EXAMPLE 1

Experimental Procedures

A. Materials

The human $sPLA_2$, rabbit anti-human $sPLA_2$ polyclonal antibody, and enzymatic and chromogenic substrates used in these experiments were supplied by Eli Lilly & Co. hen egg-white lysozyme (6× crystallized) was provided by Dr. S. C. Gill, Jr and is commercially available. The 2' $NH_2$ modified CTP and UTP were prepared according to Pieken et al. (1991) Science 253: 314–317. DNA oligonucleotides were synthesized by Operon. All other reagents and chemicals were purchased from commercial sources.

B. SELEX: 2'OH RNA

The SELEX procedure is described in detail in U.S. Pat. No. 5,270,163 and elsewhere. The DNA template used in 2'OH RNA SELEXes contained 30 random nucleotides, flanked by the N1 template 5' and 3' fixed regions (30N1 (SEQ ID NO.:1), Table I). The fixed regions include DNA primer annealing sites for PCR and cDNA synthesis as well as the consensus T7 promoter region to allow in vitro transcription. These single-stranded DNA molecules were converted into double-stranded transcribable templates by PCR amplification using the primers indicated in Table I (SEQ ID NOs.:2 and 3). PCR conditions were 50 mM KCl, 10 mM Tris-Cl, pH 9, 0.1% Triton X-100, 7.5 mM $MgCl_2$, 1 mM of each dATP, dCTP, dGTP, and dTTP, and contained 25 U/ml of Taq DNA polymerase. Transcription reactions contained 5 mM DNA template, 5 U/µl T7 RNA polymerase, 40 mM Tris-Cl (pH 8.0), 12 mM $MgCl_2$, 5 mM DTT, 1 mM spermidine, 0.002% Triton X-100, 4% PEG 8000, 2 mM each of 2'OH ATP, 2'OH GTP, 2'OH CTP, 2'OH UTP, and 0.31 mM a $^{32}P$ 2'OH ATP. SELEX binding reactions are outlined in Table I. For the binding reactions, RNA molecules were incubated with $sPLA_2$ in TBSC buffer (137 mM NaCl, 5 mM KCl, 5 mM $CaCl_2$, 10 mM Tris-HCl, pH 7.4) for 15 minutes at 37° C. Protein-RNA complexes were separated from unbound RNA by nitrocellulose filter partitioning and bound RNA was isolated from filters by phenol/urea extraction. The RNA was reverse transcribed into cDNA by AMV reverse transcriptase at 48° C. for 60 minutes in 50 mM Tris-Cl pH (8.3), 60 mM NaCl, 6 mM Mg(OAc)$_2$, 10 mM DTT, 100 pmol DNA primer, 0.4 mM each of dNTPs, and 0.4 U/µl AMV RT. PCR amplification of this cDNA resulted in approximately 500 pmol double-stranded DNA, transcripts of which were used to initiate the next round of SELEX.

C. SELEX: 2'$NH_2$ RNA

For 2'$NH_2$ SELEXes, DNA templates contained 50 random nucleotides flanked by N7 (50N7 SELEX (SEQ ID NO.:4)) or by N9 (50N9 SELEX (SEQ ID NO.:7)) 3' and 5' fixed regions shown in Table I. The RNAs transcribed from these templates contained cytidine and uridine in which the 2'OH of the ribose moiety was replaced with a $NH_2$ group.

In these SELEXes, both nitrocellulose partitioning (50N9 SELEX: rounds 6, 7, 10 and 11; 50N7 SELEX rounds 7, 8, 11 and 12) and $sPLA_2$ immobilized on beads via an anti-$sPLA_2$ polyclonal antibody (50N9 SELEX: rounds 1–5, 8 and 9; 50N7 SELEX rounds 1–6, 9 and 10) were used to separate free from bound RNA.

Polyclonal anti-$sPLA_2$ agarose beads were prepared from an ammonium sulfate precipitated, anion exchange purified immunoglobulin fraction of an $sPLA_2$ immunized rabbit. The immunoglobulins were bound to hydrazide activated agarose beads (CARBOLINK Coupling Gel, Pierce, Rockford, Ill.) according to the manufacturer's instructions. The resulting immunoglobulin density was estimated to be 1.2 mg/ml of gel. Coupling of $sPLA_2$ was accomplished by incubating 50 µl of Ab-gel with 500 µl of 2 µM $sPLA_2$ in TBSC for 2 hours at 37 ° C. The washed gel, which was resuspended in 500 µl of TBSC and stored at 4° C., had a calculated $sPLA_2$ density of 0.2 to 2 pmol/µl of gel, assuming that 1 to 10% of the Ig fraction is anti-$sPLA_2$ Ab and a stoichiometry of 2 molecules of $sPLA_2$ bound per antibody molecule.

For rounds in which immobilized $sPLA_2$ was used to partition unbound RNA from $sPLA_2$/RNA complexes, RNA was incubated with washed $sPLA_2$-gel in a siliconized column for 5 minutes at 37° C., as indicated in Table I. Unbound RNA was removed by extensive washing with TBSC. Bound RNA was eluted as two fractions; the first fraction was eluted with calcium free buffer, TBS; the second fraction was eluted with free polyclonal anti-$sPLA_2$ Ab in TBS and was processed for use in the following round. The percentage of input RNA eluted by each step is recorded in Table I. For rounds in which partitioning was accomplished by nitrocellulose filter binding (Table I), free $sPLA_2$ and RNA were incubated for 5 minutes at 37° C., filtered through TBSC prewashed nitrocellulose filters and then washed with 3 ml of TBSC.

RNA/$sPLA_2$ complexes absorbed to nitrocellulose filters and fractions eluted from immobilized $sPLA_2$ were heated at 90° C. for 5 minutes in 1% SDS, 2% b-mercaptoethanol and extracted with phenol/chloroform. The RNAs were then processed as in the 2'OH SELEXes except that 2'$NH_2$ CTP and 2'$NH_2$ UTP were substituted for CTP and UTP in transcription reactions.

D. Nitrocellulose Filter Partitioning

The nitrocellulose filter partitioning method was used as described in SELEX Patent Applications to determine the affinity of RNA ligands for $sPLA_2$ and for other promins. Filter discs (nitrocellulose/cellulose acetate mixed matrix, 0.45 µm pore size, Millipore) were placed on a vacuum manifold and washed with 5 ml of TBSC buffer under vacuum. Reaction mixtures, containing $^{32}P$ labeled RNA pools and $sPLA_2$, were incubated in TBSC for 5 minutes at 37° C., filtered, and then immediately washed with 5 ml TBSC. The filters were air-dried and counted in a Beckman liquid scintillation counter without fluor.

The equilibrium dissociation constant, $K_d$, for an RNA pool or specific ligand that binds monophasically is given by the equation $$K_d = [P_f][R_f]/[RP]$$

where,

[Rf]=free RNA concentration

[Pf]=free Protein concentration

[RP]=concentration of RNA/protein complexes $K_d$=dissociation constant

A rearrangement of this equation, in which the fraction of RNA bound at equilibrium is expressed as a function of the total concentration of the reactants, was used to calculate $K_d$s of monophasic binding curves:

$$q=(P_T+R_T+K_d-((P_T+R_T+K_d)^2-4\ P_TR_T)^{1/2})$$

q=fraction of RNA bound
[$P_T$]=total protein concentration
[$R_T$]=total RNA concentration Many ligands and evolved RNA pools yield biphasic binding curves. Biphasic binding can be described as the binding of two affinity species that are not in equilibrium. Biphasic binding data were evaluated with the equation $$q=2P_t+R_t+K_{d1}+K_{d2}-[(P_t+X_1R_1+K_{d1})^2-4P_tX_1R_t]^{1/2}-[(P_t+X_2R_t+K_{d2})^2-4P_tX_2R_t]^{1/2},$$

where $X_1$ and $X_2$ are the mole fractions of affinity species $R_1$ and $R_2$ and $K_{d1}$ and $K_{d2}$ are the corresponding dissociation constants. $K_d$s were determined by least square fitting of the data points using the graphics program Kaleidagraph (Synergy Software, Reading, Pa.).

E. Cloning and Sequencing

During the last round of SELEX, PCR of cDNA was performed with primers which contain recognition sites for the restriction endonucleases HindIII and BamHI. Using these restriction sites, the DNA sequences were inserted directionally into the pUC 18 vector. These recombinant plasmids were transformed into *E. coli* strain XL-1 Blue (Stratagene, La Jolla, Calif.). Plasmid DNA was prepared according to the alkaline hydrolysis method (Zhou et al. (1990) Biotechniques 8: 172–173) and about 100 clones were sequenced with the Sequenase sequencing kit (United States Biochemical Corporation, Cleveland, Ohio).

F. Ligand Truncation

Truncation experiments were carried out to determine the minimal sequence necessary for high affinity binding of the RNA ligands to sPLA$_2$. For 3' boundary determination, RNA ligands were 5' end-labeled with $\gamma$ $^{32}$P-ATP using T4 polynucleotide kinase. 5' boundaries were established with 3' end-labeled ligands using a $^{32}$P-pCp and T4 RNA ligase. After partial alkaline hydrolysis, radiolabeled RNA ligands were incubated with sPLA$_2$ at concentrations ranging from 0.04 nM to 28 nM and sPLA$_2$/RNA complexes were separated from unbound RNA by nitrocellulose partitioning. RNA truncates that bound with high affinity were identified on high-resolution denaturing polyacrylamide gels. For each radioactively labeled ligand, two types of ladders were generated to serve as markers: 1) a partial alkaline hydrolysis ladder, and 2) a partial RNase T1 digestion ladder.

EXAMPLE 2

RNA Ligands to sPLA$_2$

A. 2'OH SELEX

The primary objectives of the 2'OH SELEXes were 1) to generate high affinity ligands to human sPLA$_2$ and 2) to determine if a non-amplifiable, non-specific competitor could provide selection pressure for high affinity ligands under experimental conditions which, in the absence of competitor, did not detectably enrich for high affinity ligands. Experimental conditions for the Control, Competition, and Standard SELEX procedures are outlined in Table 1. The (Control) SELEX experiment was initiated with 240 nM sPLA$_2$ and a 10-fold molar excess of 2'OH RNA randomized at 30 contiguous positions, 30N1 (SEQ ID NO.:1); these conditions were maintained throughout this SELEX. A second (Competition) SELEX, in which increased stringency was imposed by a high concentration of a non-amplifiable competitor (0.5 mM tRNA), was initiated with an aliquot of the third round Control SELEX RNA. A third (Standard) SELEX, in which stringency was increased by reducing the sPLA$_2$ concentration to 12 nM, while maintaining a 10-fold molar excess of RNA, was started with an aliquot of the fifth round Control SELEX RNA.

The starting pool contained approximately 5×10$^{14}$ RNA molecules (500 pmol) and bound sPLA$_2$ with $K_d$ of 240 nM. After 12 rounds, the Standard and Competition SELEX pools bound sPLA$_2$ biphasically; the high affinity species represented about 25% of the molecules in both pools and bound with a $K_d$ of 4 nM. No improvement was observed in the affinity of the Control SELEX RNA. These results validate the non-amplifiable competitor strategy.

The three SELEXes showed no further improvement in affinity in subsequent rounds. Twelfth and fourteenth round cDNAs from the Standard and Competition SELEXes, respectively, were PCR amplified and cloned into pUC 18; 51 clones from the Standard and 34 from the Competition SELEX were sequenced. Sequences were aligned manually and are provided in Table II. The sequences from the 2'OH SELEX from 30N1 RNA are designated by ligand names with numbers only (SEQ ID NOs.:10–59).

B. 2'NH$_2$ SELEX

In the 2'NH$_2$ SELEXes, two alternate techniques were used to partition unbound RNA from sPLA$_2$/RNA complexes: nitrocellulose filtration and sPLA$_2$ immobilized on polyclonal anti-sPLA$_2$ beads as outlined in Table I. The elution of RNA from immobilized sPLA$_2$/RNA complexes was based on the observation that the binding of many ligands to sPLA$_2$ is calcium dependent and on the premise that free polyclonal antibody can compete off bound ligands.

The starting pools for both the 50N7 (SEQ ID NO.:4) and 50N9 (SEQ ID NO.:7) SELEXes contained approximately 5×10$^{14}$ RNA molecules (500 pmol) and bound sPLA$_2$ with $K_{d's}$ of 71 and 48 nM, respectively. After 11 rounds, the 50N9 SELEX pool bound sPLA$_2$ biphasically; the high affinity species which represented about 67% of the molecules, bound with a $K_d$ of 1.3 nM. Only a marginal improvement in affinity ($K_d$=17 nM) was observed for the twelfth round 50N7 SELEX. Eleventh and twelfth round cDNAs from the 50N9 and 50N7 SELEXes, respectively, were PCR amplified with primers containing restriction sites and cloned into pUC18; 40 clones from the 50N9 and 41 from the 50N7 SELEX were sequenced. Sequences were aligned manually and are shown in Table II. The sequences from the 50N9 RNA SELEX are designated by ligand names including NN (SEQ ID NOs.:60– 80) and the sequences from the 50N7 RNA SELEX are designated by ligand names including NS (SEQ ID NOs.:81–96).

C. RNA Sequences

Sequences identified by the sPLA$_2$ SELEX procedures described above are shown in Table II (SEQ ID NOs.:10–96). In the 2'OH SELEXes, 16 of 51 (Standard SELEX) and 14 of 34 (Competition SELEX) sequenced ligands were unique. A unique sequence is operationally defined as one that differs from all others by three or more nucleotides. In Table II, the RNA sequences of all 2'OH RNA ligands are shown in standard single letter code (Cornish-Bowden (1985) Nuc. Acid Res. 13: 3021–3030). These clones fall into five sequence families (I–V) and a group of unrelated sequences (Orphans); ligands in all six groups bind with high affinity. In addition, 12 of 38 (50N9) and 12 of 40 (50N7) sequenced ligands were unique (Table II). All of the 50N9 ligands that bound sPLA$_2$ with high affinity constituted a single sequence family (VI) which is the dominant family (19 of 40) of the 50N9 SELEX. Ligand NS2 which was isolated repeatedly from the 50N7 SELEX and the 2'OH Standard SELEX orphan 60 are related to family VI.

The data in Table II define consensus sequences for families I, II, III and VI (SEQ ID NOs.:97–100). The juxtaposition of the conserved sequences of family VI to the 5' fixed region and the conservation of the AGA by ligand NN2, suggest that these ligands require at least 3 nucleotides of the 5' fixed sequence for high affinity binding. Similarly, the family II alignment suggests that a 5' proximal CUC is necessary for high affinity binding; in some ligands this is a 5' fixed sequence, while in others it is an evolved sequence. Based on the juxtaposition of the conserved sequence of family I and II to the 3' fixed region an analogous logic predicts 3' boundaries within the 3' fixed region for ligands of these families.

The data in Table II also show that the distribution of sequence families I–V and orphans is different in the Standard and Competition SELEXes. Family I and V ligands occur frequently (18/51 and 9/51, respectively) in the Standard SELEX but are undetectable (0/34) in the Competition SELEX. A simple explanation for this difference is based on the observation that the high affinity binding of family I and V ligands and orphan 60 (and presumably the other orphans), unlike ligands of families II, III and IV, is calcium dependent. This correlation suggests that the free calcium was titrated by the high concentration of competitor tRNA, thus disallowing enrichment for high affinity, calcium dependent ligands.

D. Affinities

The dissociation constants for representative members of families I–VI, orphan and other ligands were determined by nitrocellulose filter binding experiments and are listed in Table III. Unlike random RNA, all tested ligands from the 2'OH SELEXes bound biphasically. Since the affinity determinations are made under conditions of protein excess, biphasic binding suggests that the ligand exists as two affinity species that are not in equilibrium, presumably these correspond to alternatively folded conformations. In most cases, the affinity of the low affinity species resembles that of random RNA which suggests that one folded conformation binds with high affinity and that all others bind like random RNA. Most high affinity species have dissociation constants from 0.2 to 2 nM which is 1200 to 120-fold improvement over random RNA.

Unlike the 2'OH ligands, the high affinity 2'NH$_2$ ligands bind monophasically. The lone exception is family VI ligand NN27 (SEQ ID NO:61) which differs from the consensus sequence in having a rigorously conserved G replaced by a U. The affinity of family VI ligands is approximately 1 nM which is about a 50-fold improvement over that of random 2'NH$_2$ RNA. The binding characteristics of the 2'OH and 2'NH$_2$ ligands demonstrate that a priori it is not possible to know if a biphasic population is a collection of biphasic binders or a mixed population of high and low affinity ligands.

EXAMPLE 3

Ligand Truncation

To determine the minimal sequence necessary for high-affinity binding to sPLA$_2$, boundary analyses were performed on representative members of Family I (ligand 2 (SEQ ID NO.:11)), Family II (ligands 72 and 721 (SEQ ID NOs.:20 and 33)), Family V (ligands 80 and 87 (SEQ ID NOs.:53 and 54)), Family VI (ligands NN41, NN11 and NN19 (SEQ ID NOs.:68, 60, and 64, respectively). Data for truncation/boundary determinations are shown in Table II (SEQ ID NOs.:101–121). The 3' boundaries of family I and II ligands are located in the 3' fixed region as is that of family V ligands. The position of the 5' boundary of family II ligands is in the 5' fixed region when the conserved CUC is fixed sequence. Similarly, the 5' boundary of family VI ligands is also in the 5' fixed region, while the 5' boundary of ligand 80 is the 5' G of the 5' fixed region. The 3' boundary of family VI ligands coincides with the 3' end of the consensus sequence.

Boundary locations were checked by determining the affinities of truncated ligands that approximate the minimal ligands. Although in general such truncates frequently bind as well as full length ligands, it is not a necessary outcome for at least two reasons. First, the boundary is primarily defined from the difference in affinity of the boundary species and the species that is one nucleotide shorter. Second, boundary experiments examine the affinity of ligands truncated on only one end, while the minimal ligand is truncated from both ends.

Binding affinities for full length and truncated ligands are shown in Table III. The truncates of ligands 2 and 87 (ligands 2.3 and 87.3, (SEQ ID NOs.:102 and 109) respectively) bind as well as their full length ligands, while truncates of 72, 72t and NN19 (72.c, 72t.2c and NN19.4, (SEQ ID NOs.:105, 106, and 117) exhibit a 5 to 10 fold loss in affinity. Also, the affinity of NN19.4 is restored to nearly full length levels by the addition of as few as six nucleotides to its 3' end (NN19.11, NN19.13, NN19.15 (SEQ ID NOs.:118, 119, and 120). While the low affinity of truncate 87.4 (SEQ ID NO.:110) confirms that the 5' G of ligands 80 and 87 is essential for high affinity binding, the high affinity of truncate 87.5 (SEQ ID NO:111) shows that the entire 5' fixed sequence is not necessary. The minimal ligand, operationally defined by the traditional boundary experiment, may include sequences that are required for an alternate function (i.e.., proper folding; the ligands must renature in the course of the experiment) or for no function at all. In other words, ligands that are shorter than the minimal ligand may bind with high affinity.

EXAMPLE 4

Specificity of RNA Ligands to Human sPLA$_2$

The affinity of sPLA$_2$ ligands 2, 72, 80, 87, NN19 and NN19.15 (SEQ ID NOs.:11, 20, 53, 54, 64, and 117, respectively) for proteins other than sPLA$_2$ was determined by nitrocellulose partitioning (Tables IV and V). Like sPLA$_2$, hen egg white lysozyme, bFGF and elastase are small, highly cationic proteins. Bovine pancreatic PLA$_2$ is an evolutionarily and structurally related enzyme. The data in Table IV show that the ligands are highly specific for sPLA$_2$. Specificity is particularly well illustrated by the affinities for bovine pancreatic PLA$_2$ which is $10^4$-fold less than that for human sPLA$_2$. These data show that in general, evolved RNA ligands to sPLA$_2$ bind to other proteins with an affinity similar to that of random RNA.

EXAMPLE 5

2'F Modification of 2'OH High Affinity Ligands

It was of interest to determine if 2'OH RNA ligands converted to a nuclease resistant form by the incorporation of 2' modified pyrimidines retained affinity for the target protein. Five 2'OH high affinity ligands to sPLA$_2$ (ligands 11tF, 72F, 73tF, 86tF and 87F (SEQ ID NOs.:37, 21, 32, 50 and 55, respectively) were transcribed with 2'F CTP and 2'UTP in place of CTP and UTP and their binding affinities determined. As shown in Table III, both qualitative and quantitative changes were observed in the binding characteristics of four ligands; whereas all five bound biphasically as 2'OH RNA, they bound monophasically as 2'F RNA and their affinity was only marginally better (2 to 5 fold) than that of the random 2'F RNA control, regardless of their 2'OH affinity. On the other hand, the binding and inhibition characteristics of ligand 87 were unchanged by 2'F modification. No degradation of this RNA was observed after incubation in 0.5× serum for 3 hours.

EXAMPLE 6

Secondary Structure of High Affinity Ligands

In favorable instances, comparative analysis of aligned sequences enables deduction of secondary structure and structure-function relationships. Nucleotides that covary according to Watson-Crick base pairing rules are apt to be paired. Sequences that vary in composition and particularly in length are considered to be unimportant for function, while highly conserved sequences are apt to be directly involved in function.

Comparative analysis of family VI sequences yields a hairpin structure with a highly conserved, asymmetrical internal loop. The terminal loop (T-loop) is variable in both length and sequence (except the first and last positions) and is not apt to be directly involved in binding. The I-loop divides the stem in two. The V-stem varies in length (3–5 nucleotide pairs) and sequence. Three of the 5 base pairs are confirmed by Watson-Crick covariation. The C-stem is absolutely conserved. In this structure, the I-loop, C-stem and single stranded tails are critical for binding.

The suggested structure for family III ligands is a two plane G-quartet with a closing double helix, the sequence of which is not conserved. Based on the limited data, the G-quartet loop sequences and a 5' single stranded sequence may be conserved.

Family II contains two very highly conserved sequences: CUUACRG and GCYGAG. Without exception, the R and Y exhibit Watson-Crick covariation which strongly suggests that they are base paired, leading to a core structure consisting of a conserved, bulged stem that has an unpaired G adjacent to the 3' end of the 3' half of the stem. This G may be a loop or a bulged nucleotide.

EXAMPLE 7

Inhibition of PLA2-Mediated Contractions

The ligands of the invention are able to selectively block PLA2-mediated contractions of guinea pig lung pleural strips. The procedure described by Snyder et al. (Journal of Pharmacology and Experimental Therapeutics (1992) 262: 1147–1153) was followed to test the ability of the ligands to inhibit PLA2-induced contraction. Ligand 19.15 (SEQ ID NO: 121) was tested in this assay and showed a dose dependent inhibition of contraction. The same ligand was tested for its ability to inhibit an arachadonic acid-mediated contraction and did not act differently than the control. This example demonstrates that the ligands of the invention specifically inhibit PLA2-mediated contraction.

EXAMPLE 8

Inhibition of the sPLA$_2$ Enzymatic Activity

To directly test the ability of the RNA ligands to inhibit sPLA$_2$ enzymatic activity the procedure described by Reynolds et al. (Anal. Biochem. (1992) 204: 190–197) was followed. Ligands NN11 (SEQ ID NO: 113), NN19 (SEQ ID NO: 114), NN19.11 (SEQ IDNO: 118), NN19.13 (SEQ IDNO: 119), NN19.14(SEQ ID NO: 120), NN19.15 (SEQ ID NO: 121), 87 (SEQ ID NO: 54), 87F (SEQ ID NO: 55), 87.7 (SEQ ID NO: 112), 721 (SEQ ID NO: 104), 861 (SEQ ID NO: 49) were tested in this assay and showed an inhibitory effect.

The inhibition and affinity data for ligands 87 and 87.7 suggest a ligand with two domains. The minimal ligand, defined by boundary analysis, corresponds to the high affinity binding domain. A second domain, appended to the binding domain, is responsible for inhibition. The inhibition function may not be sequence dependent.

TABLE I

| SELEX CONDITIONS | | |
|---|---|---|
| Random RNA | | |
| SEQ ID NO: | Name | Sequence |
| 1 | 30N1 RNA | 5' gggagcucagaauaaacgcucaa-30N-uucgacaugaggcccggauccggc 3' |
| 2 | N1 5' Primer | 5' ccgaagcttaatacgactctatagggagctcagaataaacgctcaa 3' |
| 3 | N1 3' Primer | 5' gccggatccgggcctcatgtcgaa 3' |
| 4 | 50N7 RNA* | 5' gggaggacgaugcgg-50N-cagacgacucgcccga 3' |
| 5 | N7 5' Primer | 5' taatacgactcactatagggaggacgatgcgg 3' |
| 6 | N7 3' Primer | 5' tcgggcgagtcgtcctg 3' |
| 7 | 50N9 RNA* | 5' gggaaaagcgaaucauacacaaga-50N-gcuccgccagagaccaaccgagaa 3' |
| 8 | N9 5' Primer | 5' taatacgactcactatagggaaaagcgaatcatacacaaga 3' |
| 9 | N9 3' Primer | 5' ttctcggttggtctctggcggagc 3' |

| 2'OH SELEX CONDITIONS 30N1 SELEX | | | | |
|---|---|---|---|---|
| SELEX | Round | [sPLA$_2$] | [RNA] | [tRNA] |
| Control | 1–14 | 240 nM | 2.4 uM | — |
| Standard | 1–5 | 240 nM | 2.4 uM | — |

TABLE I-continued

SELEX CONDITIONS

| Competition | 6–12<br>1–3<br>4–14 | 12 nM<br>240 nM<br>240 nM | 120 nM<br>2.4 uM<br>2.4 uM | —<br>—<br>0.5 mM |
|---|---|---|---|---|

2'NH$_2$ SELEX CONDITIONS
50N9 & 50N7 SELEX
IMMOBILIZED sPLA$_2$ PARTITIONING

| Round | sPLA2 (pmol) | RNA (pmol) | Gel Vol | Total Vol | TBSC Eluted RNA | Ab Eluted RNA |
|---|---|---|---|---|---|---|
| 1 | 0.2–2 | 468 | 1 ul | 0.5 ml | 2.6% | 1.9% |
| 2 | 0.2–2 | 100 | 1 ul | 1.0 ml | 3.0% | 2.6% |
| 3 | 0.4–4 | 345 | 2 ul | 1.0 ml | 0.1% | 0.03% |
| 4 | 0.4–4 | 540 | 2 ul | 1.0 ml | 0.05% | 0.03% |
| 5 | 2–20 | 730 | 10 ul | 1.0 ml | 0.07% | 0.03% |
| 8 | 2–20 | 90 | 10 ul | 1.0 ml | 1.0% | 0.2% |
| 9 | 2–20 | 102 | 10 ul | 0.5 ml | 2.4% | 0.3% |

NITROCELLULOSE PARTITIONING

| Round | [sPLA$_2$] | [RNA] | Vol | Net RNA bound |
|---|---|---|---|---|
| 6 | 25 nM | 373 nM | 1.5 ml | 2.1% |
| 7 | 10 nM | 100 nM | 1.5 ml | 2.1% |
| 10 | 5 nM | 50 nM | 1.5 ml | 3.8% |
| 11 | 5 nM | 50 nM | 1.5 ml | 7.0% |

*All C and U have 2'NH$_2$ substituted for 2'OH for ribose

TABLE II

| Ligands | | | | |
|---|---|---|---|---|
| Family I | | | | |
| 10 | 71 | gggagcucagaauaaacgcucaa————————UCUCAU—GCUCGUCGCACGGCGUAACCGCUAUuucgacaugaggcccggauccggc |
| 11 | 26(6) | gggagcucagaauaaacgcucaa————————UCUCAUUGCUCGCACGGCGUAACCUAUuucgacaugaggcccggauccggc |
| 12 | 3 | gggagcucagaauaaacgcucaa————————AGCUCAUCGUC—UCGCAAGGCGUAUCCUAUuucgacaugaggcccggauccggc |
| 13 | 77 | gggagcucagaauaaacgcucuaaACCUCGCCU—AU—GU—GUGUCCGUACGGCGUAUCCUAu—ucgacaugaggcccggauccggc |
| 14 | 93(3) | gggagcucagaauaaacgcucaa————————CAGCCA—AU—GUGUCCGUACGGCGUAUCCUAu—ucgacaugaggcccggauccggc |
| 15 | 95 | gggagcucagaauaaacgcucaa————————CGGUGGAU—ACCA—UCGCACGGCGUAUCCUGCuucgacaugaggcccggauccggc |
| 16 | 85 | gggagcucagaauaaacgcucaa————————AUUGCAUCAU—GUA—CCGAAGACGUAUUCUAu—ucgacaugaggcccggauccggc |
| 17 | 18 | gggagcucagaauaaacgcucaa————————AUCGCAUCAU—GUA—CCGAAGACGUAUUCUAu—ucgacaugaggcccggauccggc |
| 18 | 54 | gggagcucagaauaaacgcucaa————————AUUGCAUCAU—GUA—CCGUAAGACGUAUUCUAu—ucgacaugaggcccggauccggc |
| 19 | 14 | gggagcucagaauaaacgcucaa————————AUUGCAUCAU—GUA—CCGCAAGACGUAUCCUAuucgacaugaggcccggauccggc |
| 97 | Consensus Sequence | | | YMUCAU—GUH—YCGYAMGRCGUAUYCUAU |
| | Boundary Species | | | |
| 101 | 2 | CUCAUUGCUCGUCGCACGGCGUAACCUAUuucgacauga |
| | Truncates and Derivatives | | | |
| 102 | 2.3 | GG————UCUCAUUGCUCGUCGCACGGCGUAACCUAUuucgacaugag |
| Family II | | | | |
| 20 | 72(6) | gggagcucagaauaaacgcucaaGACCUCUG——CUUACAG——CCCG——GCUGAGACAC————uucgacaugaggcccggauccggc |
| 21 | 72F | gggagcucagaauaaacgcucaaGACCUCUG——CUUACAG——CCCG——GCUGAGACAC————uucgacaugaggcccggauccggc |
| 22 | 96(2) | gggagcucagaauaaacgcucaaGACCUCUG——CUUACAG——UUCG——GCUGAGACAC————uucgacaugaggcccggauccggc |
| 23 | 13t | gggagcucagaauaaacgcucaaUGCCUCUG——CUUACGG——GUAAU——GCCGAGACAC————uucgacaugaggcccggauccggc |
| 24 | 94 | gggagcucagaauaaacgcucaaAGUCCUCUC——CUUACGG——UUCG——CCCGAGAUA————uucgacaugaggcccgauccggc |
| 25 | 15 | gggagcucagaauaaacgcucaaGACCUCUG——CUUACAG——CCCG——GCUGAGACAU————uucgacaugaggcccggauccggc |
| 26 | 79 | gggagcucagaauaaacgcucaaGACCUCUG——CUUACAG——CCCG——GCUGAGACAC————uucgacaugaggcccggauccggc |
| 27 | 88 | gggagcucagaauaaacgcucaaGACCUCUG——CUUACAG——UCCG——GCUGAGACAC————uucgacaugaggcccggauccggc |
| 28 | 81 | gggagcucagaauaaacgcucaaGACCUCUG——CUUACAG——CCCG——GCUGAGACGC————uucgacaugaggcccggauccggc |
| 29 | 68t | gggagcucagaauaaacgcucaaGCCCUCUG——CUUACGG——CUAAU——GCCGAGACGC————uucgacaugpggcccggauccggc |
| 30 | 75 | gggagcucagaauaaacgcucaaGANCUCUG——CUUACAG——CCCG——GCUGGGACAC————uucgacaugaggcccggauccggc |
| 31 | 73t | gggagcucagaauaaacgcucaa————————CUUACAG——UUCG——GCUGAGAGACGAGACCAUACuucgacaugaggcccggauccggc |
| 32 | 73tF | gggagcucagaauaaacgcucaa————————CUUACAG——UUCG——GCUGAGAGACGAGACCAUACuucgacaugaggcccggauccggc |
| 33 | 72t(2) | gggagcucagaauaaacgcucaa————————CUUACAG——UUCG——GCUGAGACGAAGAUCGACCuucgacaugaggcccggauccggc |
| 34 | 71t(3) | gggagcucagaauaaacgcucaa————————CUUACAG—GAGAUUGCCAUCUCGCUGAGACGC————uucgacaugaggcccggauccggc |
| 35 | 1t | gggagcucagaauaaacgcucaa————————CUUACGG——UUCG——GCCGAGAAACC————uucgacaugaggcccggauccggc |
| 36 | 111(2) | gggagcucagaauaaacgcucaa————————CUUACGG——GUAAA——GCCGAGAAAAUGUAUUGC—uucgacaugaggcccggauccggc |
| 37 | 111F | gggagcucagaauaaacgcucaa————————CUUACGG——GUAAA——GCCGAGAAAAUGUAUUGC—uucgacaugaggcccggauccggc |
| 38 | 36(9) | gggagcucagaauaaacgcucaaUUGUCUUACAG————GUAAA——GCUGAGGAAUCGUU————uucgacaugaggcccggauccggc |
| 39 | 4(6) | gggagcucagaauaaacgcucaaUGUCUUACAG————GUAAA——GCCGAGAAAGUUUCC————uucgacaugaggcccggauccggc |
| 40 | 35t(3) | gggagcucagaauaaacgcucaaGGCUGGGG—UCUUUUACAG————GUAAA——GCUGAGAA————uucgacaugaggcccggauccggc |
| 41 | 89 | gggagcucagaauaaacgcucaa—AGUCUUACGG————GUAAA——GCCGAGAAAGUUUCC————uucgacaugaggcccggauccggc |
| 42 | 84t | gggagcucagaauaaacgcucaaUCAUGUC—AUUACGG————GUAAA——GCCGAGUUUC————uucgacaugaggcccggauccggc |
| 43 | 79t | gggagcucagaauaaacgcucaaAUCAUGUC—AUUACGG————GUAAA——GCCGAGUUUC————uucgacaugaggcccggauccggc |
| 98 | Consensus Sequence | CUCWR——CUUACRG————BYMV——GCYGAGA |
| | Boundary Species | | | |
| 103 | 72 | aGACCUCUG——CUUACAG————CCCG——GCUGAGACAC————uucgacaugagg |
| 104 | 72t | uaaagcucaa————CUUACAG————UUCG——GCUGAGACGAAGAUCGACCuucgacaca |
| | Truncates and Derivatives | | | |

TABLE II-continued

| | Ligands | |
|---|---|---|
| 105 | 72.c | GGGaaGACCUCUG———CUUACAG———CCCG———GCUGAGACAC———uucgacaugaggcc |
| 106 | 72t.2c | GGGauaaacgcucaa———CUUACAG———UUCG———GCUGAGACGAAGAUCGACCuucgacau |

Family III

| 44 | 34t(2) | gggagcucagaauaaacgcucaaCACGAGGGUGUGGGGUGGGCCGAGCGCCUUGuucgacaugaggcccggauccggc |
| --- | --- | --- |
| 45 | 9t | gggagcucagaauaaacgcucaacCACGGGGGUGGGGUGGGCCGAGCGCCUUGuucgacaugaggcccggauccggc |
| 46 | 6t | gggagcucagaauaaacgcucaaUGCCCUCAAUGUGGGAGGGUGGGGUGGuucgacaugaggcccggauccggc |
| 47 | 76t | gggagcucagaauaaacgcucaaCGCUCAACGCGGAGGGUGGGUGuucgacaugaggcccggauccggc |
| 48 | 83t | gggagcucagaauaaacgcucaaCGCUCAACGCGGAGGGUGGGUGuucgacaugaggcccggauccggc |
| 49 | 86t | gggagcucagaauaaacgcucaaCGCUCAUGCCAAUGCGGAGGGUGGGUGuucgacaugaggcccggauccggc |
| 50 | 86tF | gggagcucagaauaaacgcucaaCGCUCAUGCCAAUGCGGAGGGUGGGUGuucgacaugaggcccggauccggc |
| 99 | Consensus Sequence | MAYGNGGWGGGUGGGUGG |

Family IV

| 51 | 2t | gggagcucagaauaaacgcucaaUCCGGAGCUGAAAAA—CAUGCCGUUAGCCuucgacaugaggcccggauccggc |
| --- | --- | --- |
| 52 | 70t | gggagcucagaauaaacgcucaaUCCGGAGCUGAAAAA—CAUGCCGUUAGCCAuucgacaugaggcccggauccggc |

Family V

| 53 | 80(7) | gggagcucagaauaaacgcucaaGCUCUGGGAUGAUGCCCAGUGCCAGCAUCuucgacaugaggcccggauccggc |
| --- | --- | --- |
| 54 | 87(2) | gggagcucagaauaaacgcucaaGCUCUGGGAUGAUGCCCACUGCCAGCAUCuucgacaugaggcccggauccggc |
| 55 | 87F | gggagcucagaauaaacgcucaaGCUCUGGGAUGAUGCCCACUGCCAGCAUCuucgacaugaggcccggauccggc |
| | Boundary Species | |
| 107 | 80 | gggagcucagaauaaacgcucaaGCUCUGGGAUGAUGCCCAGUGCCAGCAUCuucgac |
| 108 | 87.3 | gggagcucagaauaaacgcucaaGCUCUGGGAUGAUGCCCACUGCCAGCAUCuucgac |
| | Truncates and Derivatives | |
| 109 | 87.3 | gggagcucagaauaaacgcucaaGCUCUGGGAUGAUGCCCACUGCCAGCAUCuucgacaug |
| 110 | 87.4 | gggagcucagaauaaacgcucaaGCUCUGGGAUGAUGCCCACUGCCAGCAUCuucgacaug |
| 111 | 87.5 | gggagcu———auaaacgc——CUCUGGGAUGAUGCCCACUGCCAGCAUCuucgacaug |
| 112 | 87.7 | gggagcucagaauaaacgcucaaGCUCUGGGAUGAUGCCCACUGCCAGCAUCuucgacaugGUAGCUAAACAGCUUUAGGA |

Orphan Sequences

| 56 | 1 | gggagcucagaauaaacgcucaaGCCGAACCGAAUGGAGGUGGAGGGAUUGCGuucgacaugaggcccggauccggc |
| --- | --- | --- |
| 57 | 84 | gggagcucagaauaaacgcucaaGACCACGUCCGAAACGAACACCGCCACGCAuucgacaugaggcccggauccggc |
| 58 | 90 | gggagcucagaauaaacgcucaaCCAACGACUACACCUCACGCACCAUGCCCACAACGCuucgacaugaggcccggauccggc |
| 59 | 60 | gggagcucagaauaaacgcucaaACAACGGCCCACACGGAGAUCCGAGAAAAGuucgacaugaggcccggauccggc |

Family VI

| 60 | NN11(5) | gggaaaagcgaaucaauacaagaCCGGCCGGGGAAA———CCCGAGGUCCGAGGUAACGCCAUGGCGCCCUCACCGAGUCgcuccgccagagaccaaccgagaa |
| --- | --- | --- |
| 61 | NN27 | gggaaaagcgaaucauuacaagaCCGGCCGGGGAAA———CCGAGGUCCGAUGUAACGCAUGGCGCCUCCAGUCGcuccgccagagaccaaccgagaa |
| 62 | NN16 | gggaaaagcgaaucauuacaagaCCGGCCGGGGAAA———CCGAGAUCCGAGGUAACGGGCAUGGCGCCUCCACCGAGUCGcuccgccagagaccaaccgagaa |
| 63 | NN10 | gggaaaagcgaaucauuacaagaCCGGCCGGGCCAUA———GCCGAGAUCCGAGGUUGACAACUCAGUgcuccgccagagaccaaccgaga |
| 64 | NN19 | gggaaaagcgaaucauuacaagaCCGGCCGGGCCAUU———GCCGAGAUCCGAGGUUGACAACUCGGUgcuccgccagagaccaaccgagaa |
| 65 | NN24(4) | gggaaaagcgaaucauuacaagaCCGGCCGGGCCAAGC-GCUGAGAUCCGAGAUCCAUCCAUCGGUGgcuccgccagagaccaaccgagaa |
| 66 | NN11d | gggaaaagcgaaucauuacaagaGACCGGCCCGGGUAUGUGUGUAGCCGGAGAACUGCGAACCAUGGUGCCACGgcuccgccagagaccaaccgagaa |
| 67 | NN29 | gggaaaagcgaaucauuacaagaCCGGCCGGGGUGUAGCCGGAGAACUGAACCGAGACUGCUGAACAAGGUGCCACGgcuccgccagagaccaaccgagaa |
| 68 | NN41 | gggaaaagcgaaucauuacaagaCCGGCCGGGGUGUGCCGGAGAACUGCUGAACAAGGUGCCACGgcuccgccagagaccaaccgagaa |
| 69 | NN5(2) | gggaaaagcgaaucauuacaagaCCGGCCCCCCAAUCAAGGAGAUCCGAGAAUUGUGAAUGUUUGUGAGUGAGcuccgccagagaccaaccgagaa |
| 100 | Consensus Sequence | ragaCCGGCCNGSNNNNNSCNGAGAUCCGAGG |
| | Boundary Species | |
| 113 | NN11 | aagaCCGGCCGGGGAAA———CCCGAGGUCCGAGGUAACGCA |

TABLE II-continued

| | Ligands | |
|---|---|---|
| 114 | NN19 | aagaCCGGCCGGCCGCCAUA—GCCGAGAUCCGAGGUGUUG |
| 115 | NN2 | gaGACCGGCCAGCCAAGGC—GCUGAGAUCCGAGGUUCA |
| 116 | NN41 | aagaCCGGCCCCGUGCAGCCGGAGAUCCGAGACUUGCUG |

Truncates and Derivatives

| 117 | NN19.4 | gggaaaag———————aagaCCGGCCGGCCGCCAUA—GCCGAGAUCCGAGGUGUUGA |
| 118 | NN19.11 | gggaaaag———————aagaCCGGCCGGCCGCCAUA—GCCGAGAUCCGAGGUGUUGAACGAU——————agaccaaccgagaa |
| 119 | NN19.13 | gggaaaag———————aagaCCGGCCGGCCGCCAUA—GCCGAGAUCCGAGGUGUUG————————————————agaccaaccgagaa |
| 120 | NN19.14 | gggaaaag———————aagaCCGGCCCGCCGCCAUA—GCCGAGAUCCGAGGUGUUGAACGAU——————————————ccgagaa |
| 121 | NN19.15 | gggaaaag———————aagaCCGGCCGGCCGCCAUA—GCCGAGAUCCGAGGUGUUG——————————————————————ccgagaa |
| 122 | NS2(9) | gggaggacgaugcgg*U*AGUAACGGA————UACUGAUCcGAGGUUAUAGUCACUAUAUCAUCCGUCGCcagacgacugcccga |

Other Sequences

| 70 | NN3 | gggaaaagcgaaucacauacacaagaGUGUGCGUGCAUGCGUGCGUGCGUGCAUGCGUGGUGAAAGGGGUGGGGAAGAAAAACCGCCCgcuccgccagagaccaaccgagaa |
| 71 | NN4(9) | gggaaaagcgaaucauacacaagaGUGUGCGUGCAUGCGUGCGUGCAUGCGGUGUGAAAGGUGUGAAGGACCGUGCCgcuccgccagagaccaaccgagga |
| 72 | NN1 | gggaaaagcgaaucauacacaagaCGGCGAGCAUGCAGCGGCGAGCAGGCCGAGACUGAUGGAGGGCGAGACCGUGgcuccgccagagaccaaccgagaa |
| 73 | NN6 | gggaaaagcgaaucauacacaagaCGGCGAGCAGCaCGGCGAGCAAGCGGCGAGGAGGACUGAUGGAGGCCGAGACCGCAGgcuccgccagagaccaaccgagaa |
| 74 | NN7 | gggaaaagcgaaucauacacaagaCGGCGAGCAGCaCGGCGAGCAUGCGCGAGCGGCGAGGAGGACUGAUGGAGGGCGAGACCGCAAgcuccgccagagaccaaccgagaa |
| 75 | NN22 | gggaaaagcgaaucauacacaagaCGGCGAGCAUGCGGGAGCAGGCGGCGAGGACUGAUGGAGGGCGAGACCGU*U*gcuccgccagagaccaaccgagaa |
| 76 | NN45 | gggaaaagcgaaucauacacaagaCGGCGAGCAGGCUCGCAGGCAGGAGGAGGAGGACUGAUGGAGGCCGAGACCGCGUgcuccgccagagaccaaccgagaa |
| 77 | NN40(2) | gggaaaagcgaaucauacacaagaCCCCUGAGCUCGCAGCAAGGCGGCAAGGUGCAAGGCGGAGAAAGUCGUCACAgcuccgccagagaccaaccgagaa |
| 78 | NN18 | gggaaaagcgaaucauacacaagaGGAUGGGCGACAGACACCACACCGUGCGGAAAGUGGAGAAUCCGUCAGGAgcuccgccagagaccaaccgagaa |
| 79 | NN30 | gggaaaagcgaaucuacacaagaGCCAGCGAGUGUGUGCGCACAGUGUGGCAGUGGGCGAAGUGGAGGAUUGGAGACgcuccgccagagaccaaccgagaa |
| 80 | NN39 | gggaaaagcgaaucauacacaagaCUGGUUGUGUGCGAGGAAAAAGCAUCGUGUGUAACCGAUCGUGGCAGCUCGGgcuccgccagagaccaaccgagaa |
| 81 | NS20(17) | gggaggacgaugcggAGGGUGGAUCGCGUGGAUGAAGUGAAUCCGGUGUAGCGAUGAUGUGCCcagacgacugcccga |
| 82 | NS39(3) | gggaggacgaugcggGUAGGGACACACAGACACCACACGUUCUAACAUGCCCcagacgacugcccga |
| 83 | NS38(2) | gggaggacgaugcggGUAGGGAGUAGGGAGUAGGGAGAGGGGAUCCAUCGUAACAUGCCCcagacgacugcccga |
| 84 | NS4 | gggaggacgaugcggUGAAAAGGAAAGUGAGUGUACAGCGAAUACACACUCGAAUUGGAUAAGCUUGCGUGCGCcagacgacugcccga |
| 85 | NS12(2) | gggaggacgaugcggUGAAAAGGAAAGUGAGUGAUUACAAGCGAAUACACACUCGAAUUGGAUAAGUGUCUCGGCcagacgacugcccga |
| 86 | NS27 | gggaggacgaugcggUGAAAAGGAAAUGAGAAAUGAAUGAAUGAUAAcaagagAAUGGGAAUAAGUGUCUUGGCUcagacgacugcccga |
| 87 | NS11(2) | gggaggacgaugcggGAGGGAAAGGGUGAAGGGUGAACGGAACUCCGAUAAAGCUGUACAACGUAUACGACUGCGUcagacgacugcccga |
| 88 | NS1 | gggaggacgaugcggAUAAGGAGGGAGCAAGCGAGAAAUUGAGAAGAAUCGACAUCAGUCUCGGGGcagacgacugcccga |
| 89 | NS49 | gggaggacgaugcggAUAAGGAGAUAAGGGGAUAAGGCGAACGAGAUAGGAGAUAGCCAUGUCCCcagacgacugcccga |
| 90 | NS48 | gggaggacgaugcggGCUAAGGAGCUUAGGAUGAGCAACAGACAAUGAGAUAGCAGAUGAGGCAUCACCCAUGUGCUcagacgacugcccga |
| 91 | NS13 | gggaggacgaugcggUGAGCCUUAGGAUAGGAGCAACAGAGUGAAGAGUCAGAGUGAAACUAGGGGUGCcagacgacugcccga |
| 92 | NS10 | gggaggacgaugcggUGACAAAUGACAAGUAGAAUGAGCAAGUGAUAGAUGUAGGAUGAUAGAGGACAGCCGGGGCcagacgacugcccga |
| 93 | NS14 | gggaggacgaugcggAAAUGUGUUAGUGAAAUGUGAAUGAGAGAAGAUGAGAUAGUUGAAGAUGuACAUAuAACCCnGCcagacgacugcccga |
| 94 | NS6 | gggaggacgaugcggAACuAAAAAGACAGGAGUGAUGGAGGAUUGAGAAGACAGUCAAGGUCAGAGUCUCGGGCcagacgacugcccga |
| 95 | NS18 | gggaggacgaugcggAGUAGAAGUAGAAUGUAGGAUUGAGGAUUGAAGUGCAGAGUCAGCGCGGGCcagacgacugcccga |
| 96 | NS7 | gggaggacgaugcggAGGAAAUGAAGUAACAUGAUAUAUGGAAUACGUGAUGUGGCcagacgacugcccga |

*Fixed sequences are represented by lower case lettering; evolved sequence by upper case. "—" indicates spacing for alignment. Ligands recovered from the 2'OH Competition SELEX are denoted by "t"; F indicates 2'OH ligands which contain 2'F CTP and 2'F UTP in place of CTP and UTP, respectively. Sequences that were isolated more than once, are indicated by the parenthetical number, (n), following the ligand isolate number.
• Sequence ID Number

TABLE III

| Ligand | SEQ ID NO | Kd1 | Kd2 | Mole fraction |
|---|---|---|---|---|
| A: 2'OH Ligands | | | | |
| *Family I* | | | | |
| 71 | 10 | 1.3 nM | 82 nM | 0.60 |
| 2 | 11 | 1.7 nM | 180 nm | 0.45 |
| 2.3 | 102 | 2.6 nM | 740 nM | 0.55 |
| 3 | 12 | 1.9 nM | 33 nM | 0.55 |
| 85 | 16 | 3.8 nM | 92 nM | 0.60 |
| 93 | 14 | 17.2 nM | 82 nM | 0.50 |
| 95 | 15 | 4.5 nM | 140 nM | 0.65 |
| 18 | 17 | 5.0 nM | 240 nM | 0.50 |
| 54 | 18 | 16.6 nM | 350 nM | 0.70 |
| *Family II* | | | | |
| 72 | 103 | 0.5 nM | 270 nM | 0.13 |
| 72F | 21 | 5.6 nM | | |
| 72c | 104 | 4.6 nM | 170 nM | 0.15 |
| 96 | 22 | 0.9 nM | 130 nM | 0.40 |
| 79 | 26 | 1.7 nM | 52 nM | 0.35 |
| 73t | 31 | 2.4 nM | 530 nM | 0.40 |
| 73tF | 32 | 14.0 nM | | |
| 75t | 30 | 0.9 nM | 420 nM | 0.40 |
| 72t.2c | 106 | 5.0 nM | 360 nM | 0.40 |
| 11t | 36 | 0.6 nM | 110 nM | 0.40 |
| 11tF | 37 | 7.0 nM | | |
| 4 | 39 | 0.7 nM | 300 nM | 0.55 |
| 89 | 41 | 2.5 nM | 62 nM | 0.50 |
| 35t | 40 | 2.4 nM | 170 nM | 0.65 |
| *Family III* | | | | |
| 9t | 45 | 39.4 nM | 310 nM | 0.25 |
| 6t | 46 | 28.0 nM | 1830 nM | 0.50 |
| 83t | 48 | 10.5 nM | 170 nM | 0.30 |
| 86t | 49 | 2.8 nM | 450 nM | 0.35 |
| 86tF | 50 | 12.0 nM | | |
| *Family V* | | | | |
| 80 | 53 | 1.6 nM | 300 nM | 0.40 |
| 87 | 54 | 0.8 nM | 450 nM | 0.50 |
| 87F | 55 | 1.2 nM | 840 nM | 0.50 |
| 87.3 | 109 | 0.8 nM | 720 nM | 0.40 |
| 87.4 | 110 | | 4350 nM | |
| 87.5 | 111 | 3.1 nM | 1320 nM | 0.50 |
| 87.7 | 112 | 0.8 nM | 250 nM | 0.30 |
| *Unrelated Sequence* | | | | |
| 1 | 56 | 1.4 nM | 43 nM | 0.25 |
| 60 | 59 | 0.3 nM | 200 nM | 0.20 |
| *Random RNA* | | | | |
| 30N1 | 1 | | 360 nM | |
| 30N1F | 1 | | 35 nM | |
| B: 2'NH₂ Ligands | | | | |
| *Family VI* | | | | |
| NN11 | 60 | 2.8 nM | | |
| NN27 | 61 | 0.4 nM | 150 nM | 0.2 |
| NN16 | 62 | 0.9 nm | | |
| NN10 | 63 | 0.4 nM | | |
| NN19 | 64 | 0.4 nM | | |
| NN2 | 65 | 1.2 nM | | |
| NN11d | 66 | | | |
| NN29 | 67 | 2.5 nM | | |
| NN41 | 68 | 1.2 nM | | |
| NN5 | 69 | 4.6 nM | | |
| NN19.4 | 117 | 7.3 nM | | |
| NN19.11 | 118 | 0.5 nM | | |
| NN19.13 | 119 | 2.2 nM | | |
| NN19.14 | 120 | 1.0 nM | | |
| NN19.15 | 121 | 1.7 nM | | |
| NS2 | 122 | 22.0 nM | | |
| *Other Sequences* | | | | |
| NN1 | 72 | 21 nM | | |
| NN4 | 71 | 27 nM | | |
| NN18 | 78 | 71 nM | | |
| NN22 | 75 | 36 nM | | |
| NN30 | 79 | 23 nM | | |
| NN39 | 80 | 52 nM | | |
| NN40 | 77 | 31 nM | | |
| NS1 | 88 | 42 nM | | |
| NS4 | 84 | 24 nM | | |
| NS6 | 94 | 28 nM | | |
| A: 2'NH₂ Ligands | | | | |
| NS7 | 96 | 18 nM | | |
| NS10 | 92 | 22 nM | | |
| NS11 | 87 | 16 nM | | |
| NS12 | 85 | 40 nM | | |
| NS13 | 91 | 15 nM | | |
| NS14 | 93 | 12 nM | | |
| NS18 | 95 | 52 nM | | |
| NS39 | 82 | 16 nM | | |
| NS48 | 90 | 42 nM | | |
| NS49 | 89 | 26 nM | | |
| *Random 2'NH₂ RNA* | | | | |
| 50N7 RNA | 4 | 71 nM | | |
| 50N9 RNA | 7 | 48 nM | | |

TABLE IV

Selectivity of sPLA₂ RNA Ligands
$K_d$(nM) to specified protein*

| Seq. ID # | Ligand | Lysozyme | bFGF | bpPLA2 | sPLA₂ |
|---|---|---|---|---|---|
| 11 | 2 | 1,700 | 230 | 20,000 | 1.7 |
| 20 | 72 | 1,500 | 180 | 29,000 | 0.5 |
| 53 | 80 | 2,700 | 240 | 29,000 | 1.6 |
| 54 | 87 | 2,300 | 220 | 20,000 | 0.8 |
| 1 | 30N1 | 1,650 | 270 | 22,500 | 360 |

*Standard binding experiments were performed to the specified target protein in TBSC and $K_d$'s is calculated by curve fitting. The ligands bind no better than randomized RNA (30N1) to lysozyme (hen egg-white), human basic fibroblast growth factor basic (bFGF) and bovine pancreatic PLA₂. The sPLA₂ $K_d$ that of the high affinity species.

TABLE V

Selectivity of sPLA₂ 2'NH₂RNA Ligands
$K_d$(nM) to specified protein*

| Seq. ID # | Ligand | Elastase | bFGF | C1q | IgG | sPLA₂ |
|---|---|---|---|---|---|---|
| 64 | NN19 | 40 | 210 | — | >5,000 | 1 |
| 121 | NN19.15 | 40 | 165 | 1,000 | 4,300 | 0.4 |
| 7 | 50N9 | 70 | 170 | 1,000 | >5,000 | 48 |

*Standard binding experiments were performed to the specified target protein in TBSC and $K_d$'s calculated by curve fitting. The ligands bind no better than randomized RNA (30N1) to human neutrophil elastase, human basic fibroblast growth factor (bFGF), and human immunoglobulin G (IgG and C1q).

We claim:

1. A method for identifying nucleic acid ligands and nucleic acid ligand sequences to secretory phospholipase A2 (sPLA$_2$) comprising:

a) contacting a candidate mixture of nucleic acids with sPLA$_2$, wherein nucleic acids having an increased affinity to the sPLA$_2$ relative to the candidate mixture may be partitioned from the remainder of the candidate mixture;

b) partitioning the increased affinity nucleic acids from the remainder of the candidate mixture; and c) amplifying the increased affinity nucleic acids to yield a mixture of nucleic acids enriched for nucleic acid sequences with relatively higher affinity and specificity for binding to sPLA$_2$, whereby nucleic acid ligands and nucleic acid ligand sequences of sPLA$_2$ may be identified.

2. The method of claim 1 further comprising:

d) repeating steps a), b) and c).

3. The method of claim 1 wherein said candidate mixture is comprised of single-stranded nucleic acids.

4. The method of claim 3 wherein said single-stranded nucleic acids are ribonucleic acids.

5. The method of claim 3 wherein said single-stranded nucleic acids are deoxyribonucleic acids.

6. A nucleic acid ligand to sPLA$_2$ identified according to the method of claim 1.

7. A purified and isolated non-naturally occurring nucleic acid ligand to secretory phospholipase A$_2$ (sPLA$_2$).

8. The nucleic acid ligand of claim 7 which is a ribonucleic acid ligand.

9. The RNA ligand of claim 8 wherein said RNA ligand is selected from the group consisting of the nucleotide sequences set forth in Table II, SEQ ID NOS:10–122.

10. A purified and isolated non-naturally occuring RNA ligand to sPLA$_2$ comprising the sequences selected from the group consisting of SEQ ID NOS: 97–100.

11. The ligand of claim 7 wherein said ligand comprises a chemically modified pyrimidine base selected from the group consisting of 2'- NH$_2$ pyrimidines and 2'-F pyrimidines.

\* \* \* \* \*

SEQUENCE LISTING ( 1 ) GENERAL INFORMATION:

( i i i ) NUMBER OF SEQUENCES: 122

( 2 ) INFORMATION FOR SEQ ID NO:1:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGGAGCUCAG AAUAAACGCU CAANNNNNN NNNNNNNNN NNNNNNNNN        50

NNNUUCGACA UGAGGCCCGG AUCCGGC        77

( 2 ) INFORMATION FOR SEQ ID NO:2:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCGAAGCTTA ATACGACTCT ATAGGGAGCT CAGAATAAAC GCTCAA        46

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCGGATCCG GGCCTCATGT CGAA        24

( 2 ) INFORMATION FOR SEQ ID NO:4:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:4:

GGGAGGACGA UGCGGNNNNN NNNNNNNNNN NNNNNNNNNN NNNNNNNNN        50

NNNNNNNNNN NNNNCAGAC GACUCGCCCG A        81

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TAATACGACT CACTATAGGG AGGACGATGC GG 32

( 2 ) INFORMATION FOR SEQ ID NO:6:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:6:

TCGGGCGAGT CGTCCTG 17

( 2 ) INFORMATION FOR SEQ ID NO:7:

( i ) SEQUENCE CHARACTERISTICS:
  ( A ) LENGTH: 98 base pairs
  ( B ) TYPE: nucleic acid
  ( C ) STRANDEDNESS: single
  ( D ) TOPOLOGY: linear ( i x ) FEATURE:
  ( D ) OTHER INFORMATION: ALL C'S ARE 2'-NH$_2$ cytosine ( i x ) FEATURE:
  ( D ) OTHER INFORMATION: ALL U'S ARE 2'-NH$_2$ uracil ( x i ) SEQUENCE DESCRIPTION: SEQ ID NO:7:

GGGAAAAGCG AAUCAUACAC AAGANNNNNN NNNNNNNNNN NNNNNNNNN 50

NNNNNNNNN NNNNNNNNNN NNNNGCUCCG CCAGAGACCA ACCGAGAA 98

( 2 ) INFORMATION FOR SEQ ID NO:8:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

TAATACGACT CACTATAGGG AAAAGCGAAT CATACACAAG A 41

( 2 ) INFORMATION FOR SEQ ID NO:9:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

TTCTCGGTTG GTCTCTGGCG GAGC 24

( 2 ) INFORMATION FOR SEQ ID NO:10:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:10:

GGGAGCUCAG AAUAAACGCU CAAUCUCAUG CUCGUCGCAC GGCGUAACCU 50

AUUUCGACAU GAGGCCCGGA UCCGGC 76

( 2 ) INFORMATION FOR SEQ ID NO:11:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:11:

GGGAGCUCAG AAUAAACGCU CAAUCUCAUU GCUCGUCGCA CGGCGUAACC    50

UAUUUCGACA UGAGGCCCGG AUCCGGC    77

( 2 ) INFORMATION FOR SEQ ID NO:12:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:12:

GGGAGCUCAG AAUAAACGCU CAAAGCUCAU CGUCUCGCAA GGCGUAUCCU    50

AUUUCGACAU GAGGCCCGGA UCCGGC    76

( 2 ) INFORMATION FOR SEQ ID NO:13:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:13:

GGGAGCUCAG AAUAAACGCU CAAACCUCGC CUAUGUUCGC GCGGCGUAUC    50

CUAUUCGACA UGAGGCCCGG AUCCGGC    77

( 2 ) INFORMATION FOR SEQ ID NO:14:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:14:

GGGAGCUCAG AAUAAACGCU CAACAGCCAA UGUGUCCCGU ACGGCGUAUC    50

CUAUUCGACA UGAGGCCCGG AUCCGGC    77

( 2 ) INFORMATION FOR SEQ ID NO:15:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:15:

GGGAGCUCAG AAUAAACGCU CAACGCUGGA UACCAUCGCA CGGCGUAUCC    50

UGCUUCGACA UGAGGCCCGG AUCCGGC    77

( 2 ) INFORMATION FOR SEQ ID NO:16:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:16:

GGGAGCUCAG AAUAAACGCU CAAAUUGCAU CAUGUACCGC AAGACGUAUU    50

CUAUUCGACA UGAGGCCCGG AUCCGGC    77

( 2 ) INFORMATION FOR SEQ ID NO:17:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAGCUCAG AAUAAACGCU CAAAUCGCAU CAUGUACCGC AAGACGUAUU    50

CUAUUCGACA UGAGGCCCGG AUCCGGC    77

( 2 ) INFORMATION FOR SEQ ID NO:18:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGGAGCUCAG AAUAAACGCU CAAAUUGCAU CAUGUACCGU AAGACGUAUU    50

CUAUUCGACA UGAGGCCCGG AUCCGGC    77

( 2 ) INFORMATION FOR SEQ ID NO:19:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGGAGCUCAG AAUAAACGCU CAAAUUGCAU CAUGUACCGC AAGACGUAUC    50

CUAUUUCGAC AUGAGGCCCG GAUCCGGC    78

( 2 ) INFORMATION FOR SEQ ID NO:20:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGGAGCUCAG AAUAAACGCU CAAGACCUCU GCUUACAGCC CGGCUGAGAC    50

ACUUCGACAU GAGGCCCGGA UCCGGC    76

( 2 ) INFORMATION FOR SEQ ID NO:21:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-F cytosine ( i x ) FEATURE:

(D) OTHER INFORMATION: ALL U'S ARE 2'-F uracil (x i) SEQUENCE DESCRIPTION: SEQ ID NO:21:

GGGAGCUCAG AAUAAACGCU CAAGACCUCU GCUUACAGCC CGGCUGAGAC 50

ACUUCGACAU GAGGCCCGGA UCCGGC 76

(2) INFORMATION FOR SEQ ID NO:22:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (x i) SEQUENCE DESCRIPTION: SEQ ID NO:22:

GGGAGCUCAG AAUAAACGCU CAAGACCUCU GCUUACAGUU CGGCUGAGAC 50

ACUUCGACAU GAGGCCCGGA UCCGGC 76

(2) INFORMATION FOR SEQ ID NO:23:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (x i) SEQUENCE DESCRIPTION: SEQ ID NO:23:

GGGAGCUCAG AAUAAACGCU CAAUGCCUCU GCUUACGGGU AAUGCCGAGA 50

CACUUCGACA UGAGGCCCGG AUCCGGC 77

(2) INFORMATION FOR SEQ ID NO:24:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (x i) SEQUENCE DESCRIPTION: SEQ ID NO:24:

GGGAGCUCAG AAUAAACGCU CAAAGUCCUC UCCUUACGGU UCGCCCGAGA 50

UAAUUCGACA UGAGGCCCGG AUCCGGC 77

(2) INFORMATION FOR SEQ ID NO:25:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (x i) SEQUENCE DESCRIPTION: SEQ ID NO:25:

GGGAGCUCAG AAUAAACGCU CAAGACCUCU GCUUACAGCC CGGCUGAGAC 50

AUUUCGACAU GAGGCCCGGA UCCGGC 76

(2) INFORMATION FOR SEQ ID NO:26:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (x i) SEQUENCE DESCRIPTION: SEQ ID NO:26:

GGGAGCUCAG AAUAAACGCU CAAGACCUCU GCUUACAGCU CGGCUGAGAC 50

ACUUCGACAU GAGGCCCGGA UCCGGC                                                    76

( 2 ) INFORMATION FOR SEQ ID NO:27:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GGGAGCUCAG AAUAAACGCU CAAGACCUCU GCUUACAGUC CGGCUGAGAC            50

ACUUCGACAU GAGGCCCGGA UCCGGC                                      76

( 2 ) INFORMATION FOR SEQ ID NO:28:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GGGAGCUCAG AAUAAACGCU CAAGACCUCU GCUUACAGCC CGGCUGAGAC            50

GCUUCGACAU GAGGCCCGGA UCCGGC                                      76

( 2 ) INFORMATION FOR SEQ ID NO:29:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGGAGCUCAG AAUAAACGCU CAAGGCCUCU GCUUACGGCU AAUGCCGAGA            50

CGCUUCGACA UGAGGCCCGG AUCCGGC                                     77

( 2 ) INFORMATION FOR SEQ ID NO:30:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GGGAGCUCAG AAUAAACGCU CAAGANCUCU GCUUACAGCC CGGCUGGGAC            50

ACUUCGACAU GAGGCCCGGA UCCGGC                                      76

( 2 ) INFORMATION FOR SEQ ID NO:31:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GGGAGCUCAG AAUAAACGCU CAACUUACAG UUCGGCUGAG AGAAGACGCA            50

UACUUCGACA UGAGGCCCGG AUCCGGC                                     77

( 2 ) INFORMATION FOR SEQ ID NO:32:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i x ) FEATURE:
    ( D ) OTHER INFORMATION: ALL C'S ARE 2'-F cytosine ( i x ) FEATURE:
    ( D ) OTHER INFORMATION: ALL U'S ARE 2'-F uracil ( x i ) SEQUENCE DESCRIPTION: SEQ ID NO:32:

| | | | | | |
|---|---|---|---|---|---|
| GGGAGCUCAG | AAUAAACGCU | CAACUUACAG | UUCGGCUGAG | AGAAGACGCA | 50 |
| UACUUCGACA | UGAGGCCCGG | AUCCGGC | | | 77 |

( 2 ) INFORMATION FOR SEQ ID NO:33:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

| | | | | | |
|---|---|---|---|---|---|
| GGGAGCUCAG | AAUAAACGCU | CAACUUACAG | UUCGGCUGAG | ACGAAGAUCG | 50 |
| ACCUUCGACA | UGAGGCCCGG | AUCCGGC | | | 77 |

( 2 ) INFORMATION FOR SEQ ID NO:34:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:34:

| | | | | | |
|---|---|---|---|---|---|
| GGGAGCUCAG | AAUAAACGCU | CAACUUACAG | GAGAUUCCAU | CUCGCUGAGA | 50 |
| CGCUUCGACA | UGAGGCCCGG | AUCCGGC | | | 77 |

( 2 ) INFORMATION FOR SEQ ID NO:35:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:35:

| | | | | | |
|---|---|---|---|---|---|
| GGGAGCUCAG | AAUAAACGCU | CAACUUACGG | CAGCGAUUGC | UGGCCGAGAA | 50 |
| ACCUUCGACA | UGAGGCCCGG | AUCCGGC | | | 77 |

( 2 ) INFORMATION FOR SEQ ID NO:36:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:36:

| | | | | | |
|---|---|---|---|---|---|
| GGGAGCUCAG | AAUAAACGCU | CAACUUACGG | GUAAAGCCGA | GAAAAUGUAU | 50 |
| UGCUUCGACA | UGAGGCCCGG | AUCCGGC | | | 77 |

( 2 ) INFORMATION FOR SEQ ID NO:37:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-F cytosine ( i x ) FEATURE:
        ( D ) OTHER INFORMATION: ALL U'S ARE 2'-F uracil ( x i ) SEQUENCE DESCRIPTION: SEQ ID NO:37:

```
GGGAGCUCAG  AAUAAACGCU  CAACUUACGG  GUAAAGCCGA  GAAAAUGUAU        50

UGCUUCGACA  UGAGGCCCGG  AUCCGGC                                   77
```

( 2 ) INFORMATION FOR SEQ ID NO:38:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

```
GGGAGCUCAG  AAUAAACGCU  CAAUUGUCUU  ACAGGUAAAG  CUGAGGAAUC        50

GUUUUCGACA  UGAGGCCCGG  AUCCGGC                                   77
```

( 2 ) INFORMATION FOR SEQ ID NO:39:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
GGGAGCUCAG  AAUAAACGCU  CAAUGUCUUA  CGGGUAAAGC  CGAGAAAGUU        50

UCCUUCGACA  UGAGGCCCGG  AUCCGGC                                   77
```

( 2 ) INFORMATION FOR SEQ ID NO:40:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
GGGAGCUCAG  AAUAAACGCU  CAAGGCUGGG  UCUUUUACAG  GUAAAGCUGA        50

GAAUUCGACA  UGAGGCCCGG  AUCCGGC                                   77
```

( 2 ) INFORMATION FOR SEQ ID NO: 41:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

```
GGGAGCUCAG  AAUAAACGCU  CAAAGUCUUA  CGGGUAAAGC  CGAGAAAGUU        50

UCCUUCGACA  UGAGGCCCGG  AUCCGGC                                   77
```

( 2 ) INFORMATION FOR SEQ ID NO:42:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
GGGAGCUCAG  AAUAAACGCU  CAAUCAUGUC  AUUACGGGUA  AAGCCGAGUU           50
UCUUCGACAU  GAGGCCCGGA  UCCGGC                                       76
```

( 2 ) INFORMATION FOR SEQ ID NO:43:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

```
GGGAGCUCAG  AAUAAACGCU  CAAAUCAUGU  CAUUACGGGU  AAAGCCGAGU           50
UUCUUCGACA  UGAGGCCCGG  AUCCGGC                                      77
```

( 2 ) INFORMATION FOR SEQ ID NO:44:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
GGGAGCUCAG  AAUAAACGCU  CAACACGAGG  GUGGGUGGGU  GGCCGAGCGC           50
UUGUUCGACA  UGAGGCCCGG  AUCCGGC                                      77
```

( 2 ) INFORMATION FOR SEQ ID NO:45:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
GGGAGCUCAG  AAUAAACGCU  CAACACGGGG  GUGGGUGGGU  GGCCGAGCGC           50
UUGUUCGACA  UGAGGCCCGG  AUCCGGC                                      77
```

( 2 ) INFORMATION FOR SEQ ID NO:46:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

```
GGGAGCUCAG  AAUAAACGCU  CAAUGCCUCA  UGCCAAUGUG  GGAGGGUGGG           50
UGGUUCGACA  UGAGGCCCGG  AUCCGGC                                      77
```

( 2 ) INFORMATION FOR SEQ ID NO:47:

( i ) SEQUENCE CHARACTERISTICS:
        ( A ) LENGTH: 77 base pairs ( B ) TYPE: nucleic acid
        ( C ) STRANDEDNESS: single
        ( D ) TOPOLOGY: linear ( x i ) SEQUENCE DESCRIPTION: SEQ ID NO:47:

GGGAGCUCAG AAUAAACGCU CAACGCCUCA UGCCAACGCG GGAGGGUGGG    50

UGGUUCGACA UGAGGCCCGG AUCCGGC    77

( 2 ) INFORMATION FOR SEQ ID NO:48:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGGAGCUCAG AAUAAACGCU CAACGCCUCA UGCCAACGUG GGAGCGUGGG    50

UGGUUCGACA UGAGGCCCGG AUCCGGC    77

( 2 ) INFORMATION FOR SEQ ID NO:49:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

GGGAGCUCAG AAUAAACGCU CAACGCCUCA UGCCAAUGCG GGAGGGUGGG    50

UGGUUCGACA UGAGGCCCGG AUCCGGC    77

( 2 ) INFORMATION FOR SEQ ID NO:50:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-F cytosine ( i x ) FEATURE:
        ( D ) OTHER INFORMATION: ALL U'S ARE 2'-F uracil ( x i ) SEQUENCE DESCRIPTION: SEQ ID NO:50:

GGGAGCUCAG AAUAAACGCU CAACGCCUCA UGCCAAUGCG GGAGGGUGGG    50

UGGUUCGACA UGAGGCCCGG AUCCGGC    77

( 2 ) INFORMATION FOR SEQ ID NO:51:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGGAGCUCAG AAUAAACGCU CAAUCCGGGA GCUGAAAAAC AUGCCGUUAG    50

CCGUUCGACA UGAGGCCCGG AUCCGGC    77

( 2 ) INFORMATION FOR SEQ ID NO:52:

( i ) SEQUENCE CHARACTERISTICS:

(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:52:

GGGAGCUCAG AAUAAACGCU CAAUCCGCGA GCUGAAAAAC AUGCCGUUAG    50

CCAUUCGACA UGAGGCCCGG AUCCGGC    77

(2) INFORMATION FOR SEQ ID NO:53:

(i) SEQUENCE CHARACTERISTICS:
(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:53:

GGGAGCUCAG AAUAAACGCU CAAGCUCUGG GAUGAUGCCC AGUGUCCAGC    50

AUCUUCGACA UGAGGCCCGG AUCCGGC    77

(2) INFORMATION FOR SEQ ID NO:54:

(i) SEQUENCE CHARACTERISTICS:
(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:54:

GGGAGCUCAG AAUAAACGCU CAAGCUCUGG GAUGAUGCCC ACUGUCCAGC    50

AUCUUCGACA UGAGGCCCGG AUCCGGC    77

(2) INFORMATION FOR SEQ ID NO:55:

(i) SEQUENCE CHARACTERISTICS:
(A) LENGTH: 77 base pairs
(B) TYPE: nucleic acid
(C) STRANDEDNESS: single
(D) TOPOLOGY: linear (ix) FEATURE:
(D) OTHER INFORMATION: ALL C'S ARE 2'-F cytosine (ix) FEATURE:
(D) OTHER INFORMATION: ALL U'S ARE 2'-F uracil (xi) SEQUENCE DESCRIPTION: SEQ ID NO:55:

GGGAGCUCAG AAUAAACGCU CAAGCUCUGG GAUGAUGCCC ACUGUCCAGC    50

AUCUUCGACA UGAGGCCCGG AUCCGGC    77

(2) INFORMATION FOR SEQ ID NO:56:

(i) SEQUENCE CHARACTERISTICS:
(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:56:

GGGAGCUCAG AAUAAACGCU CAAGCCGAAC CGAAUGGAGG UGGAGGGAUU    50

GCGUUCGACA UGAGGCCCGG AUCCGGC    77

(2) INFORMATION FOR SEQ ID NO:57:

5,622,828

45 46
-continued ( i ) SEQUENCE CHARACTERISTICS:
            ( A ) LENGTH: 76 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:57:

GGGAGCUCAG AAUAAACGCU CAAGACCACG UCCGAACGAA CACCGCCACG          50

CAUUCGACAU GAGGCCCGGA UCCGGC                                   76

( 2 ) INFORMATION FOR SEQ ID NO:58:

( i ) SEQUENCE CHARACTERISTICS:
            ( A ) LENGTH: 77 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:58:

GGGAGCUCAG AAUAAACGCU CAACCAACGA CACUCACGCA UUGCCCACGA          50

ACGUUCGACA UGAGGCCCGG AUCCGGC                                  77

( 2 ) INFORMATION FOR SEQ ID NO:59:

( i ) SEQUENCE CHARACTERISTICS:
            ( A ) LENGTH: 78 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:59:

GGGAGCUCAG AAUAAACGCU CAAACAACGG CCCACACGGG AGAUCCGAGA          50

AAAGUUCGAC AUGAGGCCCG GAUCCGGC                                 78

( 2 ) INFORMATION FOR SEQ ID NO:60:

( i ) SEQUENCE CHARACTERISTICS:
            ( A ) LENGTH: 99 base pairs
            ( B ) TYPE: nucleic acid
            ( C ) STRANDEDNESS: single
            ( D ) TOPOLOGY: linear ( i x ) FEATURE:
            ( D ) OTHER INFORMATION: ALL C'S ARE 2'-NH$_2$ cytosine ( i x ) FEATURE:
            ( D ) OTHER INFORMATION: ALL U'S ARE 2'-NH$_2$ uracil ( x i ) SEQUENCE DESCRIPTION: SEQ ID NO:60:

GGGAAAAGCG AAUCAUACAC AAGACCGGCC GGGGAAACCC GAGGUCCGAG          50

GUAACGCAUG GCGCCUCACC GAGUCGCUCC GCCAGAGACC AACCGAGAA          99

( 2 ) INFORMATION FOR SEQ ID NO:61:

( i ) SEQUENCE CHARACTERISTICS:
            ( A ) LENGTH: 99 base pairs
            ( B ) TYPE: nucleic acid
            ( C ) STRANDEDNESS: single
            ( D ) TOPOLOGY: linear ( i x ) FEATURE:
            ( D ) OTHER INFORMATION: ALL C'S ARE 2'-NH$_2$ cytosine ( i x ) FEATURE:
            ( D ) OTHER INFORMATION: ALL U'S ARE 2'-NH$_2$ uracil ( x i ) SEQUENCE DESCRIPTION: SEQ ID NO:61:

GGGAAAAGCG AAUCAUACAC AAGACCGGCC GGGGAAACCC GAGGUCCGAU 50

GUAACGCAUG GCGCCUCACC GAGUCGCUCC GCCAGAGACC AACCGAGAA 99

( 2 ) INFORMATION FOR SEQ ID NO:62:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:62:

GGGAAAAGCG AAUCAUACAC AAGACCGGCC GGGGAAACCC GAGAUCCGAG 50

GUAACGCAUG GCGCCUCACC GAGUCGCUCC GCCAGAGACC AACCGAGAA 99

( 2 ) INFORMATION FOR SEQ ID NO:63:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:63:

GGGAAAAGCG AAUCAUACAC AAGACCGGCC GGCGCCAUAG CCGAGAUCCG 50

AGGUUGUACG AUGACAACUC AGUGCUCCGC CAGAGACCAA CCGAGAA 97

( 2 ) INFORMATION FOR SEQ ID NO:64:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:64:

GGGAAAAGCG AAUCAUACAC AAGACCGGCC GGCGCCAUAG CCGAGAUCCG 50

AGGUGUUGAA CGAUAACUCG GUGCUCCGCC AGAGACCAAC CGAGAA 96

( 2 ) INFORMATION FOR SEQ ID NO:65:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:

(D) OTHER INFORMATION: ALL U'S ARE 2'-NH₂ uracil (xi) SEQUENCE DESCRIPTION: SEQ ID NO:65:

GGGAAAAGCG AAUCAUACAC AAGAGACCGG CCAGCCAAGG CGCUGAGAUC    50

CGAGGUUUCA GAACCCAUCG GGUUGGCUCC GCCAGAGACC AACCGAGAA    99

(2) INFORMATION FOR SEQ ID NO:66:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-NH₂ cytosine (ix) FEATURE:
        (D) OTHER INFORMATION: ALL U'S ARE 2'-NH₂ uracil (xi) SEQUENCE DESCRIPTION: SEQ ID NO:66:

GGGAAAAGCG AAUCAUACAC AAGACCGGCC CGGUAUGUAG CCGGAGAUCC    50

GAGACUUGCU GAACGAGGUG CCACGGCUCC GCCAGAGACC AACCGAGAA    99

(2) INFORMATION FOR SEQ ID NO:67:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-NH₂ cytosine (ix) FEATURE:
        (D) OTHER INFORMATION: ALL U'S ARE 2'-NH₂ uracil (xi) SEQUENCE DESCRIPTION: SEQ ID NO:67:

GGGAAAAGCG AAUCAUACAC AAGACCGGCC CGGUGUGUAG CCGGAGAUCC    50

GAGACUUGCU GAACGAGGUG CCACGGCUCC GCCAGAGACC AACCGAGAA    99

(2) INFORMATION FOR SEQ ID NO:68:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-NH₂ cytosine (ix) FEATURE:
        (D) OTHER INFORMATION: ALL U'S ARE 2'-NH₂ uracil (xi) SEQUENCE DESCRIPTION: SEQ ID NO:68:

GGGAAAAGCG AAUCAUACAC AAGACCGGCC CGGUGUGCAG CCGGAGAUCC    50

GAGACUUGCU GAACAAGGUG CCACGGCUCC GCCAGAGACC AACCGAGAA    99

(2) INFORMATION FOR SEQ ID NO:69:

(i) SEQUENCE CHARACTERISTICS:
        (A) LENGTH: 99 base pairs
        (B) TYPE: nucleic acid
        (C) STRANDEDNESS: single
        (D) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:69:

| | | | | | |
|---|---|---|---|---|---|
| GGGAAAAGCG | AAUCAUACAC | AAGACCGGCC | CCGCCAAUCA | AGGGAGAUCC | 50 |
| GAGGAAUUGG | AAUGUUUGUG | AGUGAGCUCC | GCCAGAGACC | AACCGAGAA | 99 |

( 2 ) INFORMATION FOR SEQ ID NO:70:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:70:

| | | | | | |
|---|---|---|---|---|---|
| GGGAAAAGCG | AAUCAUACAC | AAGAGUGUGC | GGUGCAUGCG | UGGUGAAAGG | 50 |
| GGGGUGGGGA | AGAAAAACCG | GCCCGCUCCG | CCAGAGACCA | ACCGAGAA | 98 |

( 2 ) INFORMATION FOR SEQ ID NO:71:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:71:

| | | | | | |
|---|---|---|---|---|---|
| GGGAAAAGCG | AAUCAUACAC | AAGAGUGUGC | GGUGCAUGCG | UGGUGAAAGG | 50 |
| UGGGUUGUGG | AGGAAGACCG | UGCCGCUCCG | CCAGAGACCA | ACCGAGAA | 98 |

( 2 ) INFORMATION FOR SEQ ID NO:72:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:72:

| | | | | | |
|---|---|---|---|---|---|
| GGGAAAAGCG | AAUCAUACAC | AAGACGGCGA | GCAUGCGGCG | AGUGGAGGGG | 50 |
| GACUGAUGGA | GGGCGAGACC | GUGUGCUCCG | CCAGAGACCA | ACCGAGAA | 98 |

( 2 ) INFORMATION FOR SEQ ID NO:73:

( i ) SEQUENCE CHARACTERISTICS:
        ( A ) LENGTH: 98 base pairs (B) TYPE: nucleic acid
(C) STRANDEDNESS: single
(D) TOPOLOGY: linear (ix) FEATURE:
(D) OTHER INFORMATION: ALL C'S ARE 2'-NH₂ cytosine (ix) FEATURE:
(D) OTHER INFORMATION: ALL U'S ARE 2'-NH₂ uracil (xi) SEQUENCE DESCRIPTION: SEQ ID NO:73:

GGGAAAAGCG AAUCAUACAC AAGACGGCGA GCAGGCGGCG AGUGGAGGAG 50

GACUGAUGGA GGGCGAGACC GCAGGCUCCG CCAGAGACCA ACCGAGAA 98

(2) INFORMATION FOR SEQ ID NO:74:

(i) SEQUENCE CHARACTERISTICS:
(A) LENGTH: 98 base pairs
(B) TYPE: nucleic acid
(C) STRANDEDNESS: single
(D) TOPOLOGY: linear (ix) FEATURE:
(D) OTHER INFORMATION: ALL C'S ARE 2'-NH₂ cytosine (ix) FEATURE:
(D) OTHER INFORMATION: ALL U'S ARE 2'-NH₂ uracil (xi) SEQUENCE DESCRIPTION: SEQ ID NO:74:

GGGAAAAGCG AAUCAUACAC AAGACGGCGA GCAAGCGGCG AGUGGAGGAG 50

GACUGAUGGA GGGCGAGACC GCAAGCUCCG CCAGAGACCA ACCGAGAA 98

(2) INFORMATION FOR SEQ ID NO:75:

(i) SEQUENCE CHARACTERISTICS:
(A) LENGTH: 98 base pairs
(B) TYPE: nucleic acid
(C) STRANDEDNESS: single
(D) TOPOLOGY: linear (ix) FEATURE:
(D) OTHER INFORMATION: ALL C'S ARE 2'-NH₂ cytosine (ix) FEATURE:
(D) OTHER INFORMATION: ALL U'S ARE 2'-NH₂ uracil (xi) SEQUENCE DESCRIPTION: SEQ ID NO:75:

GGGAAAAGCG AAUCAUACAC AAGACGGCGA GCAUGCGGCG AGUGGAGGAG 50

GACUGAUGGA GGGCGAGACC GUGUGCUCCG CCAGAGACCA ACCGAGAA 98

(2) INFORMATION FOR SEQ ID NO:76:

(i) SEQUENCE CHARACTERISTICS:
(A) LENGTH: 98 base pairs
(B) TYPE: nucleic acid
(C) STRANDEDNESS: single
(D) TOPOLOGY: linear (ix) FEATURE:
(D) OTHER INFORMATION: ALL C'S ARE 2'-NH₂ cytosine (ix) FEATURE:
(D) OTHER INFORMATION: ALL U'S ARE 2'-NH₂ uracil (xi) SEQUENCE DESCRIPTION: SEQ ID NO:76:

GGGAAAAGCG AAUCAUACAC AAGACGGCGA GCAGGCGGCG AGUGGAGGAG 50

GACUGAUGGA GGGCGAGACC GCGUGCUCCG CCAGAGACCA ACCGAGAA 98

( 2 ) INFORMATION FOR SEQ ID NO:77:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:77:

```
GGGAAAAGCG AAUCAUACAC AAGACCCCUU GAGCUCGUGA CGCAGGAGGA         50

GGGCCGAGGA GGAAAGUCGU CACAGCUCCG CCAGAGACCA ACCGAGAA           98
```

( 2 ) INFORMATION FOR SEQ ID NO:78:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:78:

```
GGGAAAAGCG AAUCAUACAC AAGAGGAUGG CGGCAAGGCG CGAAAGGGAG         50

GAUCGAGGAG GAAUCGCGUC AGGAGCUCCG CCAGAGACCA ACCGAGAA           98
```

( 2 ) INFORMATION FOR SEQ ID NO:79:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:79:

```
GGGAAAAGCG AAUCAUACAC AAGAGCCAGC GAGUGUCGAC AGUGUGGGUG         50

GAAGUGACGG GAGGAUUGGA GACGCUCCGC CAGAGACCAA CCGAGAA            97
```

( 2 ) INFORMATION FOR SEQ ID NO:80:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:80:

```
GGGAAAAGCG AAUCAUACAC AAGACUGGUU GUGCGGACCC AGUGAGUGGG         50
```

```
AGGACGUGAG  GGUGGCAGCU  GGGCUCCGCC  AGAGACCAAC  CGAGAA                                    96
```

( 2 ) INFORMATION FOR SEQ ID NO:81:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:81:

```
GGGAGGACGA  UGCGGAGGGU  GGAUCGUGGA  GGAAAAGCAU  CGUGUGUAAC               50

CGAACCGAUC  GUGG Y CAGAC  GACUCGCCCG  A                                   81
```

( 2 ) INFORMATION FOR SEQ ID NO:82:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:82:

```
GGGAGGACGA  UGCGGGUAGG  GAUGAAGUGC  GAUGUGAAUC  CGGGUGCUAG               50

CGAUGAUGUG  UGCCCCAGAC  GACUCGCCCG  A                                     81
```

( 2 ) INFORMATION FOR SEQ ID NO:83:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:83:

```
GGGAGGACGA  UGCGGGUAGG  GAGACAGACA  CACACGCGGA  AAGUAGAGCC               50

AUCGUAACAU  GCCCCCAGAC  GACUCGCCCG  A                                     81
```

( 2 ) INFORMATION FOR SEQ ID NO:84:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:84:

GGGAGGACGA UGCGGGUAGG GAUAAGCGAG UGUACAGCGA AUACGACUCG    50

GAAUGCUUGG UGCGCCAGAC GACUCGCCCG A    81

( 2 ) INFORMATION FOR SEQ ID NO:85:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:85:

GGGAGGACGA UGCGGUGAAA GAGAAAGGUU GAGAUGAUUA CAAGCGAAUU    50

GGAUAAGUGU CUGGCCAGAC GACUCGCCCG A    81

( 2 ) INFORMATION FOR SEQ ID NO:86:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:86:

GGGAGGACGA UGCGGUGAAA UGAGAAAUGG AUUGAUGAUG AUUACAAGAG    50

AAUUGGAUAA GUGUCUGGUC AGACGACUCG CCCGA    85

( 2 ) INFORMATION FOR SEQ ID NO:87:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:87:

GGGAGGACGA UGCGGGAGGG AAGGGUGGAA CGGAACUCCG AUAAAGCUGU    50

ACAAGUACGU GGGGUCAGAC GACUCGCCCG A    81

( 2 ) INFORMATION FOR SEQ ID NO:88:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:

( D ) OTHER INFORMATION: ALL C'S ARE 2'-NH$_2$ cytosine ( i x ) FEATURE:
    ( D ) OTHER INFORMATION: ALL U'S ARE 2'-NH$_2$ uracil ( x i ) SEQUENCE DESCRIPTION: SEQ ID NO:88:

GGGAGGACGA UGCGGAUAAG GAGGAGCAAG CGAGAAAUUG AGAAGUAACA     50

AGAUCGACAU GGCCCCAGAC GACUCGCCCG A     81

( 2 ) INFORMATION FOR SEQ ID NO:89:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:89:

GGGAGGACGA UGCGGAUAAG GAUAAGAUCG AACGAGAGUG AACAAAGUUA     50

AAUACAGUCU GGGGGCAGAC GACUCGCCCG A     81

( 2 ) INFORMATION FOR SEQ ID NO:90:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:90:

GGGAGGACGA UGCGGGCUAA GGGAAGACAA UGAGAUAGCA GACAAUCAAC     50

UACACCCAUG UGCGUCAGAC GACUCGCCCG A     81

( 2 ) INFORMATION FOR SEQ ID NO:91:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:91:

GGGAGGACGA UGCGGUGAGC UUAGGAUAGG AGCAACAAGU AGAGUAGAGU     50

GAUAACUAGG GUGGCCAGAC GACUCGCCCG A     81

( 2 ) INFORMATION FOR SEQ ID NO:92:

( i ) SEQUENCE CHARACTERISTICS:
        ( A ) LENGTH: 81 base pairs
        ( B ) TYPE: nucleic acid

```
           ( C ) STRANDEDNESS: single
           ( D ) TOPOLOGY: linear ( i x ) FEATURE:
           ( D ) OTHER INFORMATION: ALL C'S ARE 2'-NH₂ cytosine ( i x ) FEATURE:
           ( D ) OTHER INFORMATION: ALL U'S ARE 2'-NH₂ uracil ( x i ) SEQUENCE DESCRIPTION: SEQ ID NO:92:
```

GGGAGGACGA UGCGGUGACA AAUGAGCAAG UAGCGAUAGA UGUGAUGGAC        50

AGAGACAGCC GGGGCCAGAC GACUCGCCCG A                            81

```
( 2 ) INFORMATION FOR SEQ ID NO:93:

( i ) SEQUENCE CHARACTERISTICS:
           ( A ) LENGTH: 81 base pairs
           ( B ) TYPE: nucleic acid
           ( C ) STRANDEDNESS: single
           ( D ) TOPOLOGY: linear ( i x ) FEATURE:
           ( D ) OTHER INFORMATION: ALL C'S ARE 2'-NH₂ cytosine ( i x ) FEATURE:
           ( D ) OTHER INFORMATION: ALL U'S ARE 2'-NH₂ uracil ( x i ) SEQUENCE DESCRIPTION: SEQ ID NO:93:
```

GGGAGGACGA UGCGGAAAUG UGUUAGUGAA UGAUUGAGAG AAGAUAGAUG        50

AUGUUGAAGU CUGGCCAGAC GACUCGCCCG A                            81

```
( 2 ) INFORMATION FOR SEQ ID NO:94:

( i ) SEQUENCE CHARACTERISTICS:
           ( A ) LENGTH: 81 base pairs
           ( B ) TYPE: nucleic acid
           ( C ) STRANDEDNESS: single
           ( D ) TOPOLOGY: linear ( i x ) FEATURE:
           ( D ) OTHER INFORMATION: ALL C'S ARE 2'-NH₂ cytosine ( i x ) FEATURE:
           ( D ) OTHER INFORMATION: ALL U'S ARE 2'-NH₂ uracil ( x i ) SEQUENCE DESCRIPTION: SEQ ID NO:94:
```

GGGAGGACGA UGCGGAACUA AAAGACAGAG AGAAAACGAC AAUACGAAGU        50

ACAUAUAACC CUGGCCAGAC GACUCGCCCG A                            81

```
( 2 ) INFORMATION FOR SEQ ID NO:95:

( i ) SEQUENCE CHARACTERISTICS:
           ( A ) LENGTH: 81 base pairs
           ( B ) TYPE: nucleic acid
           ( C ) STRANDEDNESS: single
           ( D ) TOPOLOGY: linear ( i x ) FEATURE:
           ( D ) OTHER INFORMATION: ALL C'S ARE 2'-NH₂ cytosine ( i x ) FEATURE:
           ( D ) OTHER INFORMATION: ALL U'S ARE 2'-NH₂ uracil ( x i ) SEQUENCE DESCRIPTION: SEQ ID NO:95:
```

GGGAGGACGA UGCGGAAGUA GAUGAUGGAU UGAGAUGUAA GUGUCAGUAU        50

GAAGAGUCUC UGGGCCAGAC GACUCGCCCG A                            81

( 2 ) INFORMATION FOR SEQ ID NO:96:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( i x ) FEATURE:
    ( D ) OTHER INFORMATION: ALL C'S ARE 2'-NH$_2$ cytosine ( i x ) FEATURE:
    ( D ) OTHER INFORMATION: ALL U'S ARE 2'-NH$_2$ uracil ( x i ) SEQUENCE DESCRIPTION: SEQ ID NO:96:

GGGAGGACGA UGCGGAGGAA AUGAAGUAGU GAGAGUAUAA CAUGAUUAUG      5 0

AAUACGUGAU GUGGCCAGAC GACUCGCCCG A      8 1

( 2 ) INFORMATION FOR SEQ ID NO:97:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

Y MUCAUGUH Y CG Y AMGRCGU AU Y C-
UAU      2 7

( 2 ) INFORMATION FOR SEQ ID NO:98:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

CUCWRCUUAC RGB YMVGC Y G AGA      2 3

( 2 ) INFORMATION FOR SEQ ID NO:99:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

MA Y GNGGGWG GGUGGGUGG      1 9

( 2 ) INFORMATION FOR SEQ ID NO:100:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:100:

RAGACCGGCC NGSNNNNNNN SCNGAGAUCC GAGG      3 4

( 2 ) INFORMATION FOR SEQ ID NO:101:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:101:

CUCAUUGCUC GUCGCACGGC GUAACCUAUU UCGACAUGA    39

( 2 ) INFORMATION FOR SEQ ID NO:102:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:102:

GGUCUCAUUG CUCGUCGCAC GGCGUAACCU AUUCGACAU GAG    43

( 2 ) INFORMATION FOR SEQ ID NO:103:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:103:

AGACCUCUGC UUACAGCCCG GCUGAGACAC UUCGACAUGA GG    42

( 2 ) INFORMATION FOR SEQ ID NO:104:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:104:

UAAACGCUCA ACUUACAGUU CGGCUGAGAC GAAGAUCGAC CUUCGACA    48

( 2 ) INFORMATION FOR SEQ ID NO:105:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:105:

GGGAAGACCU CUGCUUACAG CCCGGCUGAG ACACUUCGAC AUGAGGCC    48

( 2 ) INFORMATION FOR SEQ ID NO:106:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:106:

GGGAUAAACG CUCAACUUAC AGUUCGGCUG AGACGAAGAU CGACCUUCGA    50

CAU    53

( 2 ) INFORMATION FOR SEQ ID NO:107:

( i ) SEQUENCE CHARACTERISTICS:
    ( A ) LENGTH: 59 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:107:

GGGAGCUCAG AAUAAACGCU CAAGCUCUGG GAUGAUGCCC AGUGUCCAGC    50

AUCUUCGAC    59

( 2 ) INFORMATION FOR SEQ ID NO:108:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

GGGAGCUCAG AAUAAACGCU CAAGCUCUGG GAUGAUGCCC ACUGUCCAGC    50

AUCUUCGAC    59

( 2 ) INFORMATION FOR SEQ ID NO:109:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

GGGAGCUCAG AAUAAACGCU CAAGCUCUGG GAUGAUGCCC ACUGUCCAGC    50

AUCUUCGACA UG    62

( 2 ) INFORMATION FOR SEQ ID NO:110:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

GGAGCUCAGA AUAAACGCUC AAGCUCUGGG AUGAUGCCCA CUGUCCAGCA    50

UCUUCGACAU G    61

( 2 ) INFORMATION FOR SEQ ID NO:111:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

GGGAGCUAUA AACGCAGCUC UGGGAUGAUG CCCACUGUCC AGCAUCUUCG    50

ACAUG    55

( 2 ) INFORMATION FOR SEQ ID NO:112:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

GGGAGCUCAG AAUAAACGCU CAAGCUCUGG GAUGAUGCCC ACUGUCCAGC  50

AUCUUCGACA UGUGUAGCUA AACAGCUUUA GGA  83

( 2 ) INFORMATION FOR SEQ ID NO:113:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:113:

AAGACCGGCC GGGGAAACCC GAGGUCCGAG GUAACGCA  38

( 2 ) INFORMATION FOR SEQ ID NO:114:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:114:

AAGACCGGCC GGCGCCAUAG CCGAGAUCCG AGGUGUUG  38

( 2 ) INFORMATION FOR SEQ ID NO:115:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:115:

GAGACCGGCC AGCCAAGGCG CUGAGAUCCG AGGUUUCA  38

( 2 ) INFORMATION FOR SEQ ID NO:116:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:116:

AAGACCGGCC CGGUGUGCAG CCGGAGAUCC GAGACUUGCU G    41

(2) INFORMATION FOR SEQ ID NO:117:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-$NH_2$ cytosine (ix) FEATURE:
        (D) OTHER INFORMATION: ALL U'S ARE 2'-$NH_2$ uracil (xi) SEQUENCE DESCRIPTION: SEQ ID NO:117:

GGGAAAAGAA GACCGGCCGG CGCCAUAGCC GAGAUCCGAG GUGUUGA    47

(2) INFORMATION FOR SEQ ID NO:118:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-$NH_2$ cytosine (ix) FEATURE:
        (D) OTHER INFORMATION: ALL U'S ARE 2'-$NH_2$ uracil (xi) SEQUENCE DESCRIPTION: SEQ ID NO:118:

GGGAAAAGAA GACCGGCCGG CGCCAUAGCC GAGAUCCGAG GUGUUGAACG    50

AUAGACCAAC CGAGAA    66

(2) INFORMATION FOR SEQ ID NO:119:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-$NH_2$ cytosine (ix) FEATURE:
        (D) OTHER INFORMATION: ALL U'S ARE 2'-$NH_2$ uracil (xi) SEQUENCE DESCRIPTION: SEQ ID NO:119:

GGGAAAAGAA GACCGGCCGG CGCCAUAGCC GAGAUCCGAG GUGUUGAGAC    50

CAACCGAGAA    60

(2) INFORMATION FOR SEQ ID NO:120:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ix) FEATURE:
        (D) OTHER INFORMATION: ALL C'S ARE 2'-$NH_2$ cytosine (ix) FEATURE:
        (D) OTHER INFORMATION: ALL U'S ARE 2'-$NH_2$ uracil (xi) SEQUENCE DESCRIPTION: SEQ ID NO:120:

```
GGGAAAAGAA  GACCGGCCGG  CGCCAUAGCC  GAGAUCCGAG  GUGUUGAACG           50

AUCCGAGAA                                                             59
```

( 2 ) INFORMATION FOR SEQ ID NO:121:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:121:

```
GGGAAAAGAA  GACCGGCCGG  CGCCAUAGCC  GAGAUCCGAG  GUGUUGCCGA           50

GAA                                                                   53
```

( 2 ) INFORMATION FOR SEQ ID NO:122:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: ALL C'S ARE 2'-NH$_2$ cytosine ( i x ) FEATURE:
        ( D ) OTHER INFORMATION: ALL U'S ARE 2'-NH$_2$ uracil ( x i ) SEQUENCE DESCRIPTION: SEQ ID NO:122:

```
GGGAGGACGA  UGCGGUAGUA  ACGGAUACUG  AUCCGAGGUU  AUAGUCACUA           50

UAUCAUCCGC  UGCGCCAGAC  GACUCGCCCG  A                                81
```